US008748368B2

(12) United States Patent
Cicardi et al.

(10) Patent No.: US 8,748,368 B2
(45) Date of Patent: *Jun. 10, 2014

(54) METHODS FOR PRESERVING ORGANS AND TISSUES

(75) Inventors: Marco Cicardi, Milan (IT); Luigi Bergamaschini, Milan (IT)

(73) Assignee: DYAX Corp., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/727,637

(22) Filed: Mar. 19, 2010

(65) Prior Publication Data

US 2011/0008762 A1    Jan. 13, 2011

Related U.S. Application Data

(60) Continuation of application No. 11/621,246, filed on Jan. 9, 2007, now Pat. No. 7,718,617, which is a division of application No. 10/456,981, filed on Jun. 6, 2003, now Pat. No. 7,166,576.

(60) Provisional application No. 60/407,004, filed on Aug. 28, 2002.

(51) Int. Cl.
*A61K 38/00* (2006.01)
*A01N 1/02* (2006.01)
*A01N 1/00* (2006.01)

(52) U.S. Cl.
USPC .............................. 514/1.1; 530/324; 435/1.1

(58) Field of Classification Search
None
See application file for complete search history.

(56) References Cited

U.S. PATENT DOCUMENTS

| | | |
|---|---|---|
| 3,682,776 A | 8/1972 | Grundmann Ekkehard et al. |
| 3,691,016 A | 9/1972 | Patel |
| 3,969,287 A | 7/1976 | Jaworek et al. |
| 4,118,481 A | 10/1978 | Schnabel et al. |
| 4,153,687 A | 5/1979 | Schnabel et al. |
| 4,179,337 A | 12/1979 | Davis et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,330,440 A | 5/1982 | Ayers et al. |
| 4,377,572 A | 3/1983 | Schwarz et al. |
| 4,399,216 A | 8/1983 | Axel et al. |
| 4,595,674 A | 6/1986 | Tschesche et al. |
| 4,609,725 A | 9/1986 | Brady et al. |
| 4,634,665 A | 1/1987 | Axel et al. |
| 4,657,893 A | 4/1987 | Krantz et al. |
| 4,845,242 A | 7/1989 | Powers et al. |
| 4,881,175 A | 11/1989 | Ladner |
| 4,946,778 A | 8/1990 | Ladner et al. |
| 5,118,668 A | 6/1992 | Auerswald et al. |
| 5,179,017 A | 1/1993 | Axel et al. |
| 5,223,409 A | 6/1993 | Ladner et al. |
| 5,260,203 A | 11/1993 | Ladner et al. |
| 5,372,933 A | 12/1994 | Zamarron |
| 5,407,915 A | 4/1995 | Fritz et al. |
| 5,409,895 A | 4/1995 | Morishita et al. |
| 5,426,224 A | 6/1995 | Lee et al. |
| 5,441,931 A | 8/1995 | Sprecher et al. |
| 5,444,156 A | 8/1995 | Veloso et al. |
| 5,576,294 A | 11/1996 | Norris et al. |
| 5,585,089 A | 12/1996 | Queen et al. |
| 5,635,187 A | 6/1997 | Bathurst et al. |
| 5,677,146 A | 10/1997 | Sprecher et al. |
| 5,693,761 A | 12/1997 | Queen et al. |
| 5,693,762 A | 12/1997 | Queen et al. |
| 5,719,041 A | 2/1998 | Lazarus et al. |
| 5,747,449 A | 5/1998 | Lasters et al. |
| 5,770,568 A | 6/1998 | Auerswald et al. |
| 5,780,265 A | 7/1998 | Dennis et al. |
| 5,786,328 A | 7/1998 | Dennis et al. |
| 5,795,865 A | 8/1998 | Markland et al. |
| 5,795,954 A | 8/1998 | Lazarus et al. |
| 5,800,385 A | 9/1998 | Demopulos et al. |
| 5,834,244 A | 11/1998 | Dennis et al. |
| 5,843,895 A | 12/1998 | Lazarus et al. |
| 5,849,992 A | 12/1998 | Meade et al. |
| 5,863,893 A | 1/1999 | Dennis et al. |
| 5,869,637 A | 2/1999 | Au-Young et al. |
| 5,874,407 A | 2/1999 | Kelley et al. |
| 5,880,256 A | 3/1999 | Dennis et al. |

(Continued)

FOREIGN PATENT DOCUMENTS

| | | |
|---|---|---|
| AT | E 275583 A1 | 4/2005 |
| CA | 2 180 950 A1 | 3/2005 |

(Continued)

OTHER PUBLICATIONS

Colman., "Plasma and tissue kallikrein in arthritis and inflammatory bowel disease" Immunopharmacology, vol. 43, pp. 103-108 (1999).
Bayes et al., "Gateways to Clinical Trials" Methods Find Exp. Clin. Pharmacol., vol. 28(3): pp. 185-206 (2006).
Extended European Search Report from European Application Serial No. 08798517.2 dated Nov. 2, 2010.
Baba, M et al., States of Tyrosyl Residues and Circular Dichroism of Kunitz Trypsin Inhibitor, J. Biochem 65 (1):113-121 (1969).
Carey et al., Advanced Organic Chemistry, 3rd Edition, Part B: Reactions and Synthesis, Plenum Press, New York: 678-686 (1990).
Chen et al., Solution Structure of a Kunitz-type Chymotrypsin Inhibitor Isolated from the Elapid Snake *Bungarus fasciatus*, J. Biological Chemistry 276:45079-45087 (2001).

(Continued)

*Primary Examiner* — Maury Audet

(74) *Attorney, Agent, or Firm* — Foley & Lardner LLP; Michel Morency; Shelby J. Walker

(57) ABSTRACT

The invention relates to a method for preserving an organ or tissue comprising contacting the organ or tissue with an effective amount of a kallikrein inhibitor and solutions useful for such a method. Also provided is a method for reducing reperfusion injury of an organ during surgery and/or following removal of the organ from a subject comprising placing the organ in an organ storage and preservative solution, wherein the solution comprises a kallikrein inhibitor.

10 Claims, 3 Drawing Sheets

(56) References Cited

U.S. PATENT DOCUMENTS

| | | | |
|---|---|---|---|
| 5,951,974 A | 9/1999 | Gilbert et al. | |
| 5,962,266 A | 10/1999 | White et al. | |
| 5,994,125 A | 11/1999 | Markland et al. | |
| 6,004,579 A | 12/1999 | Bathurst et al. | |
| 6,010,880 A | 1/2000 | Markland et al. | |
| 6,013,763 A | 1/2000 | Braisted et al. | |
| 6,057,287 A | 5/2000 | Markland et al. | |
| 6,071,723 A | 6/2000 | Markland et al. | |
| 6,087,473 A | 7/2000 | Conklin et al. | |
| 6,090,916 A | 7/2000 | Vlasuk et al. | |
| 6,103,499 A | 8/2000 | Markland et al. | |
| 6,113,896 A | 9/2000 | Lazarus et al. | |
| 6,126,933 A | 10/2000 | Warne et al. | |
| 6,159,938 A * | 12/2000 | Gyorkos et al. | 514/1.9 |
| 6,180,607 B1 | 1/2001 | Davies et al. | |
| 6,261,279 B1 | 7/2001 | Demopulos et al. | |
| 6,306,884 B1 | 10/2001 | Buckman et al. | |
| 6,333,402 B1 | 12/2001 | Markland et al. | |
| 6,407,213 B1 | 6/2002 | Carter et al. | |
| 6,423,498 B1 | 7/2002 | Markland et al. | |
| 6,472,195 B2 | 10/2002 | Hillman et al. | |
| 6,653,340 B1 * | 11/2003 | Babu et al. | 514/443 |
| 6,953,674 B2 | 10/2005 | Markland et al. | |
| 6,989,369 B2 | 1/2006 | Ladner et al. | |
| 7,064,107 B2 * | 6/2006 | Ladner et al. | 514/20.1 |
| 7,067,144 B2 | 6/2006 | Demopulos et al. | |
| 7,078,383 B2 | 7/2006 | Ley et al. | |
| 7,153,829 B2 * | 12/2006 | Ladner et al. | 514/14.9 |
| 7,166,576 B2 * | 1/2007 | Cicardi et al. | 514/20.1 |
| 7,235,530 B2 | 6/2007 | Blair et al. | |
| 7,276,480 B1 | 10/2007 | Ladner et al. | |
| 7,550,427 B2 | 6/2009 | Ley et al. | |
| 7,628,983 B2 | 12/2009 | Markland et al. | |
| 7,718,617 B2 * | 5/2010 | Cicardi et al. | 514/20.1 |
| 7,919,462 B2 | 4/2011 | Markland et al. | |
| 2001/0027180 A1 | 10/2001 | Isaacs | |
| 2003/0096733 A1 | 5/2003 | Ny et al. | |
| 2003/0113726 A1 | 6/2003 | Tsuchihashi et al. | |
| 2004/0038893 A1 | 2/2004 | Ladner et al. | |
| 2004/0053206 A1 | 3/2004 | Cicardi et al. | |
| 2004/0171794 A1 | 9/2004 | Ladner et al. | |
| 2004/0180827 A1 | 9/2004 | Chen et al. | |
| 2005/0075665 A1 | 4/2005 | Brenzel et al. | |
| 2005/0089515 A1 | 4/2005 | Ley et al. | |
| 2005/0164928 A1 | 7/2005 | Ladner et al. | |
| 2005/0222023 A1 * | 10/2005 | Hauser et al. | 514/12 |
| 2006/0069020 A1 | 3/2006 | Blair et al. | |
| 2006/0264603 A1 | 11/2006 | Markland et al. | |
| 2007/0049522 A1 | 3/2007 | Ladner et al. | |
| 2007/0117752 A1 | 5/2007 | Larsen et al. | |
| 2007/0079096 A1 | 7/2007 | Ladner | |
| 2007/0213275 A1 | 9/2007 | Clark et al. | |
| 2007/0249807 A1 | 10/2007 | Ladner et al. | |
| 2007/0253949 A1 | 11/2007 | Golz et al. | |
| 2008/0038276 A1 | 2/2008 | Sinha et al. | |
| 2008/0050716 A1 | 2/2008 | Cicardi et al. | |
| 2008/0064637 A1 | 3/2008 | Ladner et al. | |
| 2008/0076712 A1 | 3/2008 | Ladner et al. | |
| 2008/0131426 A1 | 6/2008 | Ladner et al. | |
| 2008/0139473 A1 | 6/2008 | Ladner et al. | |
| 2008/0152656 A1 | 6/2008 | Ladner et al. | |
| 2008/0188409 A1 | 8/2008 | Blair et al. | |
| 2008/0200646 A1 | 8/2008 | Ladner et al. | |
| 2008/0221031 A1 | 9/2008 | Blair et al. | |
| 2008/0226655 A1 | 9/2008 | Ladner et al. | |
| 2008/0260752 A1 | 10/2008 | Ladner et al. | |
| 2008/0299050 A1 | 12/2008 | Bortz et al. | |
| 2009/0062195 A1 | 3/2009 | Ladner et al. | |
| 2009/0075887 A1 | 3/2009 | Mcpherson | |
| 2009/0082267 A1 | 3/2009 | Ladner et al. | |
| 2009/0105142 A1 | 4/2009 | Moscicki | |
| 2009/0117130 A1 | 5/2009 | Ladner et al. | |
| 2009/0123475 A9 | 5/2009 | Siegel | |
| 2009/0215119 A1 | 8/2009 | Ladner | |
| 2009/0221480 A1 | 9/2009 | Blair et al. | |
| 2009/0227495 A1 | 9/2009 | Blair et al. | |
| 2009/0233852 A1 | 9/2009 | Blair et al. | |
| 2009/0234009 A1 | 9/2009 | Blair et al. | |
| 2009/0247452 A1 | 10/2009 | Ellis et al. | |
| 2009/0264350 A1 | 10/2009 | Blair et al. | |
| 2010/0034805 A1 | 2/2010 | Ladner et al. | |
| 2010/0183625 A1 | 7/2010 | Sternlicht | |

FOREIGN PATENT DOCUMENTS

| | | | |
|---|---|---|---|
| DE | 695 33 742 A2 | 1/2006 | |
| EP | 0132732 A2 | 2/1985 | |
| EP | 0255011 | 2/1988 | |
| EP | 0285123 A2 | 10/1988 | |
| EP | 0307592 A2 | 3/1989 | |
| EP | 0401508 | 12/1990 | |
| EP | 0486001 A1 | 5/1992 | |
| EP | 0621870 B1 | 5/1997 | |
| EP | 0621871 B1 | 7/1997 | |
| EP | 739 355 B1 | 9/2004 | |
| EP | 1484339 A2 | 12/2004 | |
| WO | WO8910374 A1 | 11/1989 | |
| WO | 902809 A1 | 3/1990 | |
| WO | WO9206111 A1 | 4/1992 | |
| WO | WO9309233 A2 | 5/1993 | |
| WO | 9314120 | 7/1993 | |
| WO | 9314121 | 7/1993 | |
| WO | WO 93/14122 | 7/1993 | |
| WO | WO 9521601 * | 1/1995 | A61K 38/00 |
| WO | WO9518830 A2 | 7/1995 | |
| WO | 95/21601 A2 | 8/1995 | |
| WO | WO 95/21601 | 8/1995 | |
| WO | 98/52976 A1 | 11/1998 | |
| WO | WO99/63090 A1 | 12/1999 | |
| WO | WO 00/14235 | 3/2000 | |
| WO | 00/34317 A2 | 6/2000 | |
| WO | 0114424 A2 | 3/2001 | |
| WO | WO0179480 A1 | 10/2001 | |
| WO | WO03066824 A1 | 8/2003 | |
| WO | WO 03/103475 | 12/2003 | |
| WO | WO2004/019968 A1 | 3/2004 | |
| WO | 2004/062646 A1 | 7/2004 | |
| WO | 2004/062689 A1 | 7/2004 | |
| WO | 2005/021557 A2 | 3/2005 | |
| WO | 2005/075665 A2 | 8/2005 | |
| WO | 2006066878 A1 | 6/2006 | |
| WO | 2006089005 A2 | 8/2006 | |
| WO | 2007079096 A2 | 7/2007 | |
| WO | 2009026334 A2 | 2/2009 | |
| WO | 2009026539 A1 | 2/2009 | |
| WO | 2009/102927 A1 | 8/2009 | |

OTHER PUBLICATIONS

Chung et al., GenBank, Accession #P03952 (1986).
Han, Eun D. Reversal of the Increased Vascular Permeability in C1 Inhibitor Deficient Mice: Therapeutic Approaches, International Immunopharmacology 2(9):1315 Abstract 176 (2002).
Han, Eun D. et al., Increased Vascular Permeability in C1 Inhibitor-Deficient Mice Mediated by the Bradykinin Type 2 Receptor, J. Clinical Investigation 109(8):1057-1063 (2002).
Gonzalez-Quevedo, T. et al., The Synthetic Kunitz Domain Protein DX88 to Treat Angioedema in Patients with Hereditary Angioedema, International Immunopharmacology 2(9):1318 Abstract 205 (2002).
Lumry et al, Interim Results of EDEMA2, a Multicenter, Open-Label, Repeat-Dosing Study of Intravenous and Subcutaneous Administration of Ecallantide (DX-88) in Hereditory Angioedema. J. Allergy and Clinical Immunology 117(2)(Suppl. 1):S179 Abstract 699 (2006).
Mann et al., Hemostasis and Thrombosis, Chapter 10, 2nd Edition, Basic Principles and Clinical Practice: 148-161 (1987).
March, Jerry, Advanced Organic Chemistry, 3rd Edition, Reactions, Mechanisms, and Structure, John Wiley and Sons, New York: 396-398; 1057-1060; 1099-1100 (1985).
Mathews, C.K., et al., Biochemistry, The Benjamin Cummins Publishing Co., Inc. Redwood City CA: 208-212 (1990).
McConnell et al., New Leupeptin Analogues: Synthesis and Inhibition Data, J. Med. Chem. 33:86-93 (1990).

(56) References Cited

OTHER PUBLICATIONS

The Merck Index: 145, 263, 427, 428, 1183, and 1184 (1989).
Robbins, K.C. et al., Hemostasis and Thrombosis, Chapter 21, 2nd Edition, Basic Principles and Clinical Practice: 340-357 (1987).
Rossi, E. et al., The Synthetic Peptide DX88 Binds to Endothelial Cells In Vitro and Retains the Inhibitory Activity on Kallikrein, International Immunopharmacology 2(9):1313, Abstract 142 (2002).
Scatchard, George, The Attractions of Proteins for Small Molecules and Ions, Ann. NY Acad. Sci, 51:660-672 (1949).
Schecther et al., On the Size of the Active Site on Proteases, I Papain, Biochemical and Biophysical Research Communications 27(2):157-162 (1967).
Schecther et al, On the Active Site of Proteases, III Mapping the Active Site of Papain; Specific Peptide Inhibitors of Papain, Biochemical and Biophysical Research Communications 32(5):898-902 (1968).
Schmaier et al., Hemostasis and Thrombosis, Chapter 2, 2nd Edition, Basic Principals and Clinical Practice: 18-38 (1987).
Communication received in EP Patent No. 1 484 339, dated Sep. 29, 2005.
International Search Report received in PCT/US07/63703, dated Dec. 21, 2007.
Communication received in EP Patent Application 03757339.1, dated Apr. 23, 2008.
PCT International Search Report dated Jul. 21, 2008 and issued in PCT/US05/34335.
PCT Written Opinion dated Jul. 21, 2008 and issued in PCT/US05/34335.
Attwood, The Babel of Bioinformatics; Science, vol. 290, pp. 471-473 (2000).
Skolnick and Fetrow, From Genes to Protein Structure and Function: Novel Applications of Computational Approaches in the Genomic Era; Trends in Biotechnology, vol. 18, pp. 34-39 (2000).
Wendel et al., Lower Cardiac Troponin T Levels in Patients Undergoing Cardiopulmonary Bypass and Receiving High-Dose Aprotinin Therapy Indicate Reduction of Perioperative Myocardial Damage; Journal of Thoracic Cardiovascular Surgery, vol. 109, No. 6, pp. 1164-1172 (1995).
Extended European Search Report dated Apr. 1, 2009, which includes the European Search Report and the European Search Opinion from European Application No. 08018863.4.
Adelman et al., "Proteolysis of Platelet Glycoprotein Ib by Plasmin Is Facilitated by Plasmin Lysine-Binding Regions," Blood, 68:1280-1284 (1986).
Albrecht et al., "Elastase Inhibition by the Inter-α-Trypsin Inhibitor and Derived Inhibitors of Man and Cattle," Hoppe-Seyler's Z. Physiol. Chem., 364:1697-1702 (1983).
Albrecht et al., "Kunitz-Type Proteinase Inhibitors Derived by Limited Proteolysis of the Inter-α-Trypsin Inhibitor, IX [1-8]," Hoppe-Seyler's Z. Physiol. Chem. 364:1703-1708 (1983).
Anba et al., "Improving the stability of a foreign protein in the periplasmic space of *Escherichia coli*," Biochimie, 70:727-733 (1988).
Angliker et al., "The synthesis of lysylfluoromethanes and their properties as inhibitors of trypsin, plasmin and cathepsin B," Biochem. J., 241:871-875 (1987).
Atherton et al., "Peptide synthesis. Part 2. Procedures for Solid-phase Synthesis using Nα-Fluorenylmethoxycarbonylamino-acids on Polyamide Supports. Synthesis of Substance P and of Acyl Carrier Protein 65-74 Decapeptide," J. Chem. Soc. Perkin Trans., 1:538-546 (1981).
Auerswald et al., "Expression, Isolation and Characterization of Recombinant [Arg15,Glu52] Aprotinin," Bio. Chem. Hoppe-Seyler, 369:(Suppl)27-35 (1988).
Balduyck et al., "Human Urinary Proteinase Inhibitor: Inhibitory Properties and Interaction with Bovine Trypsin," Bio. Chem. Hoppe-Seyler, 366:9-14 (1985).
Baneyx and Georgiou, "In Vivo Degradation of Secreted Fusion Proteins by the *Escherichia coli* Outer Membrane Protease OmpT" J. Bacteriol. 172:491-494 (1990).

Baneyx and Georgiou, "Construction and Characterization of *Escherichia coli* Strains Deficient in Multiple Secreted Proteases: Protease III Degrades High-Molecular-Weight Substrates In Vivo," J. Bacteriol., 173:2696-2703 (1991).
Berndt et al., "Designed Replacement of an Internal Hydration Water Molecule in BPTI: Structural and Functional Implications of a Glycine-to-Serine Mutation," Biochem. 32:4564-4570 (1993).
Bhoola et al., "Bioregulation of Kinins: Kallikreins, Kininogens, and Kininases," Pharmacological Reviews, 44:1-80 (1992).
Browne et al. "Expression of Recombinant Human Plasminogen and Aglycoplasminogen in HeLa Cells," GeneBank, Accession No. M74220 (1991).
Broze et al., "Regulation of Coagulation by a Multivalent Kunitz-Type Inhibitor," Biochem. 29:7539-7546 (1990).
Brus et al., "Disease Severity is Correlated With Plasma Clotting and Fibrinolytic and Kinin-Kallikrein Activity in Neonatal Respiratory Distress Syndrome," Pediatr. Res., 41:120-127 (1997).
Budavari, ed., Merck Index, 11th Edition, ISBN 911910-28-X, entries 923, 1745, 2740, 7425 (1989).
Chung et al., "Human Plasma Prekallikrein, a Zymogen to a Serine Protease That Contains Four Tandem Repeats," GenBank, Accession No. P03952 (1995).
Colman et al., "Activation of the Kallikrein-Kinin System in Arthritis and Enterocolitis in Genetically Susceptible Rats: Modulation by a Selective Plasma Kallikrein Inhibitor," Proc. Assoc. Am. Physicians, 109:10-22 (1997).
Cumming and Nimmo, "Hemodynamic, Renal, and Hormonal Actions of Aprotinin in an Ovine Model of Septic Shock," Crit. Care Med., 20:1134-1139 (1992).
Currie, B. "Design and Synthesis of a Bicyclic Non-Peptide β-Bend Mimetic of Enkephalin," Tetrahedron, 49:3489-3500 (1993).
DeLa Cadena et al., "Role of Kallikrein-Kinin System in the Pathogenesis of Bacterial Cell Wall-Induced Inflammation and Enterocolitis," Transact. Assoc. Am. Physicians, 105:229-237 (1992).
DeLa Cadena et al., "Inhibition of Plasma Kallikrein Prevents Peptidoglycan-induced Arthritis in the Lewis Rat," FASEB J., 9:446-452 (1995).
Dennis and Lazarus, "Kunitz Domain Inhibitors of Tissue Factor-Factor VIIa, (I. Potent Inhibitors Selected from Libraries by Phage Display)," J. Biol. Chem., 269:22129-22136 (1994).
Dennis and Lazarus, "Kunitz Domain Inhibitors of Tissue Factor-Factor VIIa, (II. Potent and Specific Inhibitors by Competitive Phage Selection)," J. Biol. Chem., 269:22137-22144 (1994).
Dennis et al., "Potent and Selective Kunitz Domain Inhibitors of Plasma Kallikrein Designed by Phage Display," J. Biol. Chem. 270:25411-25417 (1995).
Diaz et al., "The Design of Water Soluble β-Sheet Structure Based on a Nucleation Strategy," Tetrahedron, 49:3533-3534 (1993).
DiMaio et al., "A new class of potent thrombin inhibitors that incorporates a scissile pseudopeptide bond," FEBS Lett. 282(1):47-52 (1991).
Eigenbrot et al., "Structural Effects Induced by Removal of a Disulfide-Bridge: The X-Ray Structure of the C30A/C51A Mutant of Basic Pancreatic Trypsin Inhibitor at 1.6 Å," Protein Engineering, 3:591-598 (1990).
Ellis et al., "The Urokinase Receptor: Involvement in Cell Surface Proteolysis and Cancer Invasion," Ann. NY Acad. Sci., 667:13-31 (1992).
Fidler and Ellis, "The Implications of Angiogensis for the Biology and Therapy of Cancer Metastasis," Cell, 79:185-188 (1994).
Fields and Noble, "Solid Phase Peptide Synthesis Utilizing 9-fluorenylmethoxycarbonyl Amino Acids," Int. J. Pep. Pro. Res., 35:161-214 (1990).
Fraedrich et al., "Reduction of Blood Transfusion Requirement in Open Heart Surgery by Administration of High Doses of Aprotinin-Preliminary Results," Thorac. Cardiovasc. Surg., 37:89-91 (1989).
Freidinger et al., "Protected Lactam-Bridged Dipeptides for Use as Conformational Constraints in Peptides," J. Org. Chem., 47:104-109 (1982).
Gardell, "The Search for the Ideal Thrombolytic Agent: Maximize the Benefit and Minimize the Risk," Toxicol. Pathol. 21(2):190-198 (1993).

(56) References Cited

OTHER PUBLICATIONS

Girard et al., "Functional Significance of the Kunitz-type Inhibitory Domains of Lipoprotein-Associated Coagulation Inhibitor," Nature, 338:518-520 (1989).
Girard et al., "Structure of the Human Lipoprotein-associated Coagulation Inhibitor Gene," J. Biol. Chem. 266:5036-5041 (1991).
Hoover et al., "Amino Acids of the Recombinant Kringle 1 Domain of Human Plasminogen That Stabilize Its Interaction with ω-Amino Acids," Biochemistry, 32:10936-10943 (1993).
Hortin and Trimpe, "Allosteric Changes in Thrombin's Activity Produced by Peptides Corresponding to Segments of Natural Inhibitors and Substrates," J. Biol. Chem., 266:6866-6871 (1991).
Hostomsky et al., "Solid-Phase Assembly of Cow Colostrum Trypsin Inhibitor Gene," Nucleic Acids Res., 15:4849-4856 (1987).
Hynes et al., "X-ray Crystal Structure of the Protease Inhibitor Domain of Alzheimer's Amyloid β-Protein Precursor," Biochemistry, 32:10936-10943 (1993).
Kemp and Bowen, "Synthesis of Peptide-Functionalized Diacylaminoepindolidiones," Tetrahedron Letts., 29:5077-5080 (1988).
Kido et al., "Protease-Specificity of Kunitz Inhibitor Domain of Alzheimer's Disease Amyloid Protein Precursor," Biochem. & Biophys. Res. Comm., 167:716-721 (1990).
Kido et al., "Kunitz-type Protease Inhibitor Found in Rat Mast Cells," J. Biol. Chem. 263:18104-18107 (1988).
Kirchhoff et al., "A Major Human Epididymis-Specific cDNA Encodes a Protein With Sequence Homology to Extracellular Proteinase Inhibitors," Biol. Reprod. 45:350-357 (1991).
Kline et al., "Hirulog Peptides with Scissile Bond Replacements Resistant to Thrombin Cleavage," Biochem. Biophys. Res. Commun., 177:1049-1055 (1991).
Kurjan and Herskowitz, "Structure of a Yeast Pheromone Gene (MFα): A Putative α-Factor Precursor Contains Four Tandem Copies of Mature α-Factor," Cell, 30:933-943 (1982).
Laskowski and Kato, "Inhibitors with Class-Specific Reactive Sites," Ann. Rev. Biochem. 49:599-626 (1980).
Leatherbarrow and Salacinski, "Design of a Small Peptide-Based Proteinase Inhibitor by Modeling the Active-Site Region of Barley Chymotrypsin Inhibitor 2," Biochemistry, 30:10717-10721 (1991).
Ley et al., "Obtaining a Family of High-Affinity, High-Specificity Protein Inhibitors of Plasmin and Plasma Kallikrein," Molecular Diversity, 2:119-124 (1996).
Lohmann and Marshall, "Plasmin-and Plasminogen-Activator Inhibitors After Excimer Laser Photorefractive Keratectomy: New Concept in Prevention of Postoperative Myopic Regression and Haze," Refract. Corneal. Surg., 9:300-302 (1993).
Lucas et al., "The Binding of Human Plasminogen to Fibrin and Fibrinogen," J. Biol. Chem., 258:4249-4256 (1983).
MacGilchrist et al., "Effect of the Serine Protease Inhibitor, Aprotinin, on Systematic Haemodynamics and Renal Function in Patients with Hepatic Cirrhosis and Ascites," Clin. Sci., 87:329-335 (1994).
Markland et al., "Selection for Protease Inhibitors Using Bacteriophage Display," Methods Enzymol., 267:28-51 (1996).
Markland et al., "Iterative Optimization of High-Affinity Protease Inhibitors Using Phage Display. 1. Plasmin," Biochemistry, 35:8045-8057 (1996).
Markland et al., "Iterative Optimization of High-Affinity Protease Inhibitors Using Phage Display. 2. Plasma Kallikrein and Thrombin," Biochemistry 35:8058-8067 (1996).
McConnell et al., "New Leupeptin Analogues: Synthesis and Inhibition Data," J. Med. Chem. 33:86-93 (1990).
Merrifield, R., "Solid Phase Peptide Synthesis. I. The Synthesis of a Tetrapeptide," J. Amer. Chem. Soc., 85:2149-2154 (1963).
Merrifield, B., "Solid Phase Synthesis," Science, 232:341-347 (1986).
Miyajima et al., "Secretion of Mature Mouse Interleukin-2 by Saccharomyces cerevisiae: Use of a General Secretion Vector Containing Promoter and Leader Sequences of the Mating Pheromone α-Factor," Gene, 37:155-161 (1985).

Monteseirin et al., "Plasma Kallikrein Amidolytic Activity in Bronchial Asthma," Allergol. Immunopathol. (Madr), 20:211-214 (1992).
Naess et al., "Effects of a Combined Drug Regimen on Tumour Necrosis Factor and Plasma Kallikrein Activity in Experimental Endotoxaemia," Eur. J. Surg., 160:77-86 (1994).
Nagai et al., "Bicyclic Turned Dipeptide (BTD) as a β-Turn Mimetic: its Design, Synthesis and Incorporation into Bioactive Peptides," Tetrahedron, 49:3577-3592 (1993).
Nagai and Sato, "Synthesis of a Bicyclic Dipeptide with the Shape of β-Turn Central Part," Tetrahedron Lett., 26 (5):647-650 (1985).
Neuhaus et al., "Effect of Aprotinin on Intraoperative Bleeding and Fibrinolysis in Liver Transplantation," Lancet, 2:924-925 (1989).
Novotny et al., "Purification and Characterization of the Lipoprotein-Associated Coagulation Inhibitor from Human Plasma," J. Biol. Chem. 264:18832-18837 (1989).
Okamoto et al., "A Finding of Highly Selective Synthetic Inhibitor of Plasma Kallikrein; Its Action to Bradykinin Generation, Intrinsic Coagulation and Experimental DIC," Agents Actions Suppl., 38(I):198-205 (1992).
O'Reilly et al., "Angiostatin: A Novel Angiogenesis Inhibitor That Mediates the Suppression of Metastases by a Lewis Lung Carcinoma," Cell, 79:317-328 (1994).
Park and Tulinsky, "Three Dimensional Structure of the Kringle Sequence: Structure of Prothrombin Fragment 1," Biochem., 25:3977-3982 (1986).
Putterman, C., "Aprotinin Therapy in Septic Shock," Acta Chir. Scand., 155:367 (1989).
Sartor et al., "Selective Kallikrein-Kinin System Activation in Inbred Rats Differentially Susceptible to Granulomatous Enterocolitis," Gastroenterology 110:1467-1481 (1996).
Schmidt et al., "A male accessory gland peptide with protease inhibitory activity in Drosophila funebris," Swiss-Prot., Accession No. P11424 (1992).
Schnabel et al., "Aprotinin: Preparation by Partial Desulphurization of Aprotinin by Means of Raney Nickel and Comparison with Other Aprotinin Derivatives," Biol. Chem. Hoppe-Seyler, 367:1167-1176 (1986).
Sheppard and Williams, "Acid-labile resin linkage agents for use in solid phase peptide synthesis," Int. J. Peptide Protein Res., 20:451-454 (1982).
Sheridan et al., "A Multicenter Trial of the Use of the Proteolytic Enzyme Inhibitor Aprotinin in Colorectal Surgery," Dis. Colon Rectum, 32:505-508 (1989).
Sprecher et al., "Molecular Cloning, Expression, and Partial Characterization of a Second Human Tissue-Factor-Pathway Inhibitor," Proc. Natl. Acad. Sci. USA, 91:3353-3357 (1994).
Stadnicki et al., "Activation of the Kallikrein-Kinin System in Indomethacin-Induced Enterocolitis in Genetically Susceptible Rats," J. Invest. Med., 44:229A (1996).
Stadnicki et al., "Selective Plasma Kallikrein Inhibitor Attenuates Acute Intestinal Inflammation in Lewis Rat," Dig. Dis. Sci., 41:912-920 (1996).
Tian et al., "Synthesis of optically pure Cα-methyl-arginine," Int. J. Peptide Protein Res., 40:119-126 (1992).
van der Logt et al., "Intron-Exon Organization of the Human Gene Coding for the Lipoprotein-Associated Coagulation Inhibitor: The Factor Xa Dependent Inhibitor of the Extrinsic Pathway of Coagulation," Biochem. 30:1571-1577 (1991).
van Dijl et al., "Signal peptidase I of Bacillus subtilis: patterns of conserved amino acids in prokaryotic and eukaryotic type I signal peptidases," EMBO J., 11:2819-2828 (1992).
Varadi and Patthy, "Location of Plasminogen-Binding Sites in Human Fibrin(ogen)," Biochem., 22:2440-2446 (1983).
Varadi and Patthy, "Segment of Fibrinogen is in a Region Essential for Plasminogen Binding by Fibrin Fragment E," Biochem., 23:2108-2112 (1984).
Vedvick et al., "High-Level Secretion of Biologically Active Aprotinin From the Yeast Pichia pastoris," J. Ind. Microbiol. 7:197-201 (1991).
Wade et al., "Solid-Phase Synthesis of α-Human Atrial Natriuretic Factor: Comparison of the Boc-Polystyrene and Fmoc-Polyamide Methods," Biopolymers, 25:S21-37 (1986).

(56) References Cited

OTHER PUBLICATIONS

Wagner et al., "High Level Expression, Purification, and Characterization of the Kunitz-Type Protease Inhibitor Domain of Protease Nexin-2/Amyloid β-Protein Precursor," Biochem. Biophys. Res. Comm., 186:1138-1145 (1992).
Wilson et al., "The Calculation and Synthesis of a Template Molecule," Tetrahedron, 49:3655-3663 (1993).
Wun et al., "Cloning and Characterization of a cDNA Coding for the Lipoprotein-associated Coagulation Inhibitor Shows that it Consists of Three Tandem Kunitz-type Inhibitory Domains," J. Biol. Chem., 263:6001-6004 (1988).
International Search Report from International Application No. PCT/US03/17802, dated Oct. 30, 2003.
European Communication from European Application No. 03791557.6, dated Oct. 29, 2007.
Worthy et al., "Current Status Review Kallikreins and Kinins: mediators in inflammatory joint disease" Int. J. Exp. Pathol. 71:587-601 (1990).
Extended European Search Report for European Application Serial No. 10180486.2 dated Feb. 15, 2011.
Extended European Search Report for European Application Serial No. 10180484.7 dated Mar. 9, 2011.
Kobayashi, et. al., "Amended structure of side chains in a cell wall mannan from *Candida albicans* serotype A strain grown in yeast extract-Sabouraud liquid medium under acidic conditions: detection of the branched side chains corresponding to antigenic factor 4.", FEMS Microbiol Lett.;152(2):235-42 (Jul. 15, 1997).
Longa et al., "Reversible middle cerebral artery occlusion without craniectomy in rats" Stroke 20 (1): 84-91 (1989).
Mattheakis et al. "An in vitro polysome display system for identifying ligands from very large peptide libraries" Proc. Natl. Acad. Sci. USA 91:9022 (1994).
McCarty, "Crystal-induced inflammation of the joints," Annual Reviews of Medicine, vol. 21, pp. 357-366 (1970).
Morishita, et al., "Novel factor Xa and plasma kallikrein inhibitory-activities of the second Kunitz-type inhibitory domain of urinary trypsin inhibitor" Thromb Res, 73(3-4): p. 193-204 (1994).
Murkin et al., "Aprotinin significantly decreases bleeding and transfusion requirements in patients receiving aspirin and undergoing cardiac operations," J. Thorac. Cardiovasc. Surg., vol. 107, pp. 554-561 (1994).
Ngo et al., "The protein folding problem and tertiary structure prediction, Chapter 14: Computational complexity protein structure prediction, and the Levinthal paradox," pp. 433-440 and 492-495 only (1994).
Ngo, et al., "Computational Complexity, Protein Structure Prediction, and the Levinthal Paradox", The Protein Folding Problem and Tertiary Structure Prediction, Chapter 14, pp. 433-440 and 492-495 only (1994).
Ning, et. al., "Production of recombinant humanized anti-HBsAg Fab fragment from *Pichia pastoris* by fermentation.", J Biochem Mol Biol. ;38(3):294-9. (May 31, 2005).
Nwariaku, et al., "Effect of a bradykinin antagonist on the local inflammatory response following thermal injury" Burns, 22:324-327 (1996). (Abstract only).
Phillips, "The challenge of gene therapy and DNA dellicery," J. Pharm. Pharmacology, vol. 53, pp. 1169-1174 (2001).
Pitt et al., "Rabbit monoarticular arthritis as a model for intra-articular drug injections. The local action of administered cortisol and a-1 proteinase inhibitor," Agents and Actions, vol. 15, No. 5-6, abstract online, retrieved from internet <URl:http://www.springerlink.com/content/j82860503948741/p> (Dec. 1984).
Powers et al., "Expression of Single-Chain Fv-Fc Fusions in *Pichia pastoris*", J. Immunol. Methods. 251:123-35 (2001).
Rahman et al., "Identification and functional importance of plasma kallikrein in the synovial fluids of patients with rheumatoid, psoriatic, and osteoarthritis," Annals of the Rheumatic Diseases, vol. 54, pp. 345-350 (1995).
Ren, et al., "Inflammatory Models of Pain and Hyperalgesia" ILAR J. 40(3): 111-118 (1999).
Roberts et al., "Directed evolution of a protein: seleciton of potent neurtophil elastase inhibitor displayed on M13 fusion phage," PNAS USA, vol. 89, pp. 2429-2433 (1992).
Roberts et al., "Protease inhibitor display M13 phage: selection of high-affinity neurtophil elastase inhibitors," Gene, vol. 121, pp. 9-15 (1992).
Schaffirzel et al. "Ribosome display: an in vitro method for selection and evolution of antibodies from libraries" J Immunol Methods. 231(1-2):119-35 (1999).
Schmid-Elsaesser, et al., "A critical reevaluation of the intraluminal thread model of focal cerebral ischemia: evidence of inadvertent premature reperfusion and subarachnoid hemorrhage in rats by laser-Doppler flowmetry" Stroke 29 (10): 2162-70 (1989).
Schopf, "IDEC-114 (IDEC)" Curr Opin Investig Drugs, 2(5):635-8 (2001). (Abstact only).
Schwartz et al., "Stability studies on derivatives of the bovine trypsin inhibitor," Biochemistry, vol. 26, pp. 3544-3551 (1987).
Sharma, et al. "The kinin antagonist hoe 140 reduces acute paw oedema in rats caused by carrageenan, bradykinin and kaolin" Inflammopharmacology 6,9-17 (1998).
Shibuya, et. al., "Primary Structure of Guinea Pig Plasma Prekallikrein", Immunopharmacology, vol. 45 (1-3), p. 127-34, Abstract p. 131, Fig 1, 2 (1999).
Siebeck et al., "Inhibition of plasma kallikrein with aprotinin in porcine endotoxin shock," J. Trauma, vol. 34, pp. 193-198 (1993).
Silverberg et al. "The Contact System and Its Disorders," in Blood: Principles and Practice of Hematology, Handin R. et al., eds. J B. Lippincott Co., Philadelphia, (1995).
Slootstra et al. "Structural aspects of antibody-antigen interaction revealed through small random peptide libraries", Molecular Diversity,1, 87-96 (1996).
Smith, "Filamentous fusion phage: novel expression vectors that display cloned antigens on the virion surface" Science 228:1315-1317 (1985).
Smith, BJ. et al. "Prolonged in vivo residence times of antibody fragments associated with albumin" Bioconjug Chem 12(5):750-756 (2001).
Stultz, et al. "Structural analysis based on state-space modeling." Protein Sci. 2:305-314 (1993).
Takahashi, et al., "Production of humanized Fab fragment against human high affinity IgE receptor in *Pichia pastoris*" Biosci Biotechnol Biochem 64(10):2138-44 (2000).
Tamura, et al., "Focal cerebral ischaemia in the rat: 1. Description of technique and early neuropathological consequences following middle cerebral artery occlusion" J Cereb Blood Flow Metab 1: 53-60 (1981).
Tomlinson, et al. "The repertoire of human germline VH sequences reveals about 50 groups of VH segments with different hypervariable loops"J. Mol. Biol. 227:776-798 (1992).
Tomlinson et al. "Structural repertoire of the human Vk domain" EMBO J. 14(18):4628-3 (1995).
Tschesche et al., "Semisynthetic engineering of proteinase inhibitor homologues," Biochim. Biophys. Acta, vol. 913, pp. 97-101 (1987).
Uebel,"Die behandlung con kniegelenksarthrosen mit trasylol," Langenbacks Arch. Chir., vol. 325, pp. 356-358 (1969).
Urlaub et al., "Isolation of Chinese hamster cell mutants deficient in dihydrofolate reductase activity", Proc. Natl. Acad. Sci. USA 77:4216-4220 (1980).
Wang et al., "Monitoring of heparin-induced anticoagulation with kaolin-activated clotting time in cadiac surgical patients treated with aprotinin," Anesthesiology, vol. 77, pp. 1080-1084 (1992).
Watson, et al., "Induction of reproducible brain infarction by photochemically initiated thrombosis" Ann Neurol17: 497-504 (1985).
Wells, "Addivity of Mutational Effects in Proteins", Biochemistry, vol. 29 (37), pp. 8509-8517 (1990).
Wood, "Hemostatic Drugs" New England Journal of Medicine, Drug Therapy, 339(4):245-253 (1998).
Worthy, K. et al., "Kallikreins and Kinins: Mediators in Inflammatory Joint Disease?", International Review of Experimental Pathology, pp. 587-601, vol. 71, No. 4, Blackwell Scientific, Oxford GB (Aug. 1, 1990).

(56) References Cited

OTHER PUBLICATIONS

Zuraw B.L. et al., "Clinical practice. Hereditary angioedema" N Engl J Med 359, 1027-1036, (2008).
Abdel-Salam, et. al., "Expression of mouse anticreatine kinase (MAK33) monoclonal antibody in the yeast *Hansenula polymorpha*", Appl. Microbiol. Biotechnol, vol. 56, p. 157-164 (2001).
Adams et al: "The role of viscosupplementation with hylan G-F 20 (Synvisc(R)) in the treatment of osteoarthritis of the knee: a Canadian multicenter trial comparing hylan G-F 20 alone, hylan G-F 20 with non-steroidal anti-inflammatory drugs (NSAIDs) and NSAIDs alone", Osteoarthritis and Cartilage, Bailliere Tindall, London, GB, vol. 3, No. 4, pp. 213-225, (Dec. 1, 1995).
Asano M. et al., "Effects of a nonpeptide bradykinin B2 receptor antagonist, FR167344, on different in vivo animal models of inflammation", Br J Pharmacol, vol. 122, p. 1436-1440 (1997).Asano M. et al., Br J Pharmacol, vol. 122, p. 1436-1440 (1997).
Beckmann et al., "Preparation of chemically 'mutated' aprotinin homologues by semisynthesis-P1 substitutions change inhibitory specificity," Eur. J. Biochem., vol. 176, pp. 675-682 (1988).
Beech et al., "Further characterisation of a thromboembolic model of stroke in the rat" Brain Res, vol. 895, p. 18-24 (2001).
Berge, S.M., et al., "Pharmaceutical salts", J. Pharm. Sci. 66:1-19 (1977).
Bergthorsdottir et al., "Signals that initiate somatic hypermutation of B cell in vitro", J. Immunol., p. 166:2228 (2001).
Bird et al. "Single chain antigen binding proteins", Science 242:423-426 (1988).
Bork, "Powers and pitfalls in sequence analysis: the 70% hurdle," Genome Research, vol. 10, pp. 398-400 (2000).
Bowdish K, et. al., "Yeast expression of a catalytic antibody with chorismate mutase activity.", J Biol Chem.; 266 (18):11901-8 (Jun. 25, 1991).
Bowie et al. "Deciphering the message in protein sequences: tolerance to amino acid substitutions." Science 247:1306-1310 (1990).
Brenner, "Errors in genome annotation," Trends in Genetics, vol. 15, No. 4, pp. 132-133 (1999).
Brinkmann et al., "Design of an aprotinin variant with inhibitory activity against chymotrypsin and cathepsin G by recombinant DNA technology," Biol. Chem. Hoppe-Seyler, vol. 371, pp. 43-52 (1990).
Buchan et al., "A new model of temporary focal neocortical ischemia in the rat", Stroke 23 (2): 273-9 (1992).
Burton et al. "Human Antibody Effector Function", Adv. Immunol. 51:1-84 (1992).
Carpenter et al., "Rational design of stable lyophilized protein formulations: theory and practice," Parmaceutical Biotechnology, vol. 13, pp. 109-133 (2002).
Casati et al., "Cardiopulmonary support and physiology—tranexamic acid compared with high-dose aprotinin in primary elective heart operations: effects on perioperative bleeding and allogeneic transfusions," The Journal of Thoracic and Cardiovascular Surgery, vol. 120, pp. 520-527 (2000).
Chen et al., "A model of focal ischemic stroke in the rat: reproducible extensive cortical infarction", Stroke 17 (4): 738-43 (1986).
Chen et al., "Refined 2-5 A X-ray Crystal Structure of the Complex Formed by Porcine Kallikrein A and the Bovine Pancreatic Trypsin Inhibitor—Crystallization, Patterson Search, Structure Determination, Refinement, Structure and Comparison with its Components and with the Bovine Trypsin-Pancreatic Trypsin Inhibitor Complex" J. Mol. Biol., 164:283-311 (1983).
Chouthia et al. "Canonical structures for the hypervariable regions of immunoglobulins." (1987) J. Mol. Biol. 196:901-917 (1987).
Chouthia et al. "Structural Repertoire of the Human VH Segments", J. Mol. Biol. 227:799-817 (1992).
Colman, et al., "Contact System: A Vascular Biology Modulator With Anticoagulant, Profibrinolytic, Antiadhesive, and Proinflammatory Attributes" Blood, 90, 3819-3843 (1997).
Colman et al., Hemostasis and Thrombosis Basic Principles and Clinical Practice, Chapter 1, 2nd Edition, 3-17 (1987).

Corpet, et al. "Recent improvements of the ProDom database of protein domain families" Nucl. Acids Res. 27:263-267 (1999).
De Campos, et al., "Antioedematogenic and antinociceptive actions of NPC 18521, a novel bradykinin B2 receptor antagonist", Eur J Pharmacol316, 277-286 (1996).
De Haard, et al. "A large non-immunized human Fab fragment phage library that permits rapid isolation and kinetic analysis of high affinity antibodies". J. Biol. Chem 274:18218-30, (1999).
De Wildt, et al., "Characterization of human variable domain antibody fragments against the U1 RNA-associated A protein, selected from a synthetic and patient-derived combinatorial V gene library" Eur J Immunol. 26(3):629-39 (1996).
De Wildt, et al. "Antibody arrays for high-throughput screening of antibody-antigen interactions", Nat. Biotechnol. 18:989-994 (2000).
Doerks et al., "Protein annotation: detective work for function prediction," Trends in Genetics, vol. 14, No. 6, pp. 248-250 (1998).
Dufton, "Protein inhibitors and dendrotoxins," Eur. J. Biochem., vol. 153, pp. 647-654. (1985).
Edqvist, et al., "Production of functional IgM Fab fragments by *Saccharomyces cerevisiae*", J Biotechnol 20 (3):291-300 (1991).
Fife, et al, "Cartilage matrix glycoprotein is present in serum in experimental canine osteoarthritis" J Clin Invest. 84(5): 1432-1439 (1989).
Fredrich et al., "A new animal model of venous thrombosis in rats with low flow conditions in the venous blood stream" Blood Coagul Fibrinolysis. 5(2):243-8 (1994).
Goldenberg et al., "Circular and circularly permuted forms of bovine pancreatic trypsin inhibitor," J. Mol. Biol., vol. 165, pp. 407-413 (1983).
Gomez-Jorge et al., "The Double-Tuck Model: A New Animal Model of Arterial Thrombosis" J. Vasco Inter. Rad. 9 (4): 633-638 (1998).
Grimaldi et al., "Trasylol in the treatment of acute arthritis due to microcrystals," Reumatismo, vol. 23, No. 5, pp. 217-221, (1971) (Abstract only).
Hanes et al., "Picomolar affinity antibodies from a fully synthetic naive library selected and evolved by ribosome display" Nat Biotechnol. 18:1287-92 (2000).
Hanes et al., "Selecting and evolving functional proteins in vitro by ribosome display" Methods Enzymol. 328:404-30 (2000).
Hoogenboom et al. "Natural and designer binding sites made by phage display technology" Immunol Today 2:371-8 (2000).
Hoogenboom et al., "Antibody phage display technology and its applications" Immunotechnology 4:1-20 (1998).
Horwitz, et. al., "Secretion of functional antibody and Fab fragment from yeast cells.", Proc Natl Acad Sci U S A. 85 (22):8678-82 (Nov. 1988).
Huge et al. "A model to investigate postoperative ileus with strain gauge transducers in awake rats" J Surg Res. 74 (2):112-8 (1998). (Abstact Only).
Huston et al. "Protein engineering of antibody binding sites: Recovery of specific activity in anti-digoxin single-chain Fv analogue produced in *Escherichia coli*", Proc. Natl. Acad. Sci. USA 85:5879-5883 (1988).
Jefferis et al., "IgG-Fc-mediated effector functions: Molecular definition of interaction site for effector ligands and the role of gylcosylation", Immunol. Rev. 163:59-76, (1998).
Kabet, et al. Sequences of Proteins of Immunological Interest, Fifth Edition, U.S. Dept. of Health and Human Services, NIH Publication No. 91-3242 (1991).
Kantor, et al., "The experimental animal models for assessing treatment of restenosis" Cardiovasc Radiat Med. 1 (1):48-54 (1999).
Kaplan, et. al., "A Prealbumin Activator of Preallirrein. 3. Appearance of Chemotactic Activity for Human Neutrophils by the conversion of Human Prekallikrein", J. Exp. Med. vol. 135(1), p. 81-97; p. 92 Fig 10, p. 93 (1972).
Kaufman, et al., "Amplification and expression of sequences cotransfected with a modular dihydrofolate reductase complementary dna gene", Mol. Biol. 159:601 621 (1982).

(56) References Cited

OTHER PUBLICATIONS

Kanppik et al., "Fully synthetic human combinatorial antibody libraries (HuCAL) based on modular consensus frameworks and CDRs randomized with trinucleotides", J. Mol. Biol. 296:57-86 (2000).

Ko, et. al., "Biotransformation of uridine monophosphate (UMP) and glucose to uridine diphosphate-glucose (UDPG) by *Candida saitoana* KCTC7249 cells." Appl Biochem Biotechnol.; 60(1):41-8 (Jul. 1996).

T. Hori, et al., "Liver graft pretreated in vivo or ex vivo by γ-amino butyric acid receptor regulation," Journal of Surgical Research 182 (2013) 166-175.

\* cited by examiner

```
5AOX1
--------------------------------->                                    BstB I
CG ACT TTT AAC GAC AAC TTG AGA AGA TCA AAA AAC AAC TAA TTA TTC GAA

ACG     ATG AGA TTC CCA TCT ATC TTC ACT GCT GTT TTG TTC GCT GCT
         M   R   F   P   S   I   F   T   A   V   L   F   A   A

TCC TCT GCT TTG GCT GCT CCA GTT AAC ACC ACT ACT GAA GAC GAG ACT
 S   S   A   L   A   A   P   V   N   T   T   T   E   D   E   T

GCT CAA ATT CCT GCT GAG GCT GTC ATC GGT TAC TCT GAC TTG GAA GGT
 A   Q   I   P   A   E   A   V   I   G   Y   S   D   L   E   G

GAC TTC GAC GTC GCT GTT TTG CCA TTC TCT AAC TCT ACT AAC AAC GGT
 D   F   D   V   A   V   L   P   F   S   N   S   T   N   N   G

TTG TTG TTC ATC AAC ACT ACC ATC GCT TCT ATC GCT GCT AAG GAG GAA
 L   L   F   I   N   T   T   I   A   S   I   A   A   K   E   E

GGT GTT TCC CTC GAG AAG AGA GAG GCT ATG CAC TCT TTC TGT GCT TTC
 G   V   S   L   E   K   R   E   A   M   H   S   F   C   A   F

AAG GCT GAC GAC GGT CCG TGC AGA GCT GCT CAC CCA AGA TGG TTC TTC
 K   A   D   D   G   P   C   R   A   A   H   P   R   W   F   F

AAC ATC TTC ACG CGT CAA TGC GAG GAG TTC ATC TAC GGT GGT TGT GAG
 N   I   F   T   R   Q   C   E   E   F   I   Y   G   G   C   E

GGT AAC CAA AAC AGA TTC GAG TCT CTA GAG GAG TGT AAG AAG ATG TGT
 G   N   Q   N   R   F   E   S   L   E   E   C   K   K   M   C
                            EcoR I
ACT AGA GAC TAG TAA GAA TTC GCC TTA GAC ATG ACT GTT CCT CAG TTC
 T   R   D   *   *                                    <--------
                                                              3'AOX1
AAG TTG GGC ACT TAC GAG AAG
------------------------------
          3' AOX1
```

```
SEQ ID 2:    MHSFCAFKA-DDGPCRAAHPRWFFNIFTRQCEEFIYGG
SEQ ID 4:    MHSFCAFKA-DDGPCKANHLRFFFNIFTRQCEEFSYGG
SEQ ID 5:    MHSFCAFKA-DDGHCKANHQRFFFNIFTRQCEEFTYGG
SEQ ID 6:    MHSFCAFKA-DDGHCKANHQRFFFNIFTRQCEQFTYGG
SEQ ID 7:    MHSFCAFKA-DDGHCKASLPRFFFNIFTRQCEEFIYGG
SEQ ID 8:    MHSFCAFKA-DDGHCKANHQRFFFNIFTRQCEEFSYGG
SEQ ID 9:    MHSFCAFKA-DDGHCKGAHLRFFFNIFTRQCEEFIYGG
SEQ ID 10:   MHSFCAFKA-DDGRCKGAHLRFFFNIFTRQCEEFIYGG
SEQ ID 11:   MHSFCAFKA-DGGRCRGAHPRWFFNIFTRQCEEFSYGG
SEQ ID 12:   MHSFCAFKA-DDGPCRAAHPRWFFNIFTRQCEEFSYGG
SEQ ID 13:   MHSFCAFKA-DVGRCRGAHPRWFFNIFTRQCEEFSYGG
SEQ ID 14:   MHSFCAFKA-DVGRCRGAQPRFFFNIFTRQCEEFSYGG
SEQ ID 15:   MHSFCAFKA-DDGSCRAAHLRWFFNIFTRQCEEFSYGG
SEQ ID 16:   MHSFCAFKA-EGGSCRAAHQRWFFNIFTRQCEEFSYGG
SEQ ID 17:   MHSFCAFKA-DDGPCRGAHLRFFFNIFTRQCEEFSYGG
SEQ ID 18:   MHSFCAFKA-DDGHCRGALPRWFFNIFTRQCEEFSYGG
SEQ ID 19:   MHSFCAFKA-DSGNCRGNLPRFFFNIFTRQCEEFSYGG
SEQ ID 20:   MHSFCAFKA-DSGRCRGNHQRFFFNIFTRQCEEFSYGG
SEQ ID 21:   MHSFCAFKA-DGGRCRAIQPRWFFNIFTRQCEEFSYGG
SEQ ID 22:   MHSFCAFKA-DDGRCRGAHPRWFFNIFTRQCEEFSYGG

SEQ ID 2: (con't.)    CEGNQ--NRFESLEECKKMCTRD
SEQ ID 4: (con't.)    CGGNQ--NRFESLEECKKMCTRD
SEQ ID 5: (con't.)    CGGNQ--NRFESLEECKKMCTRD
SEQ ID 6: (con't.)    CAGNQ--NRFESLEECKKMCTRD
SEQ ID 7: (con't.)    CGGNQ--NRFESLEECKKMCTRD
SEQ ID 8: (con't)     CGGNQ--NRFESLEECKKMCTRD
SEQ ID 9: (con't.)    CEGNQ--NRFESLEECKKMCTRD
SEQ ID 10:(con't.)    CEGNQ--NRFESLEECKKMCTRD
SEQ ID 11:(con't.)    CGGNQ--NRFESLEECKKMCTRD
SEQ ID 12:(con't.)    CGGNQ--NRFESLEECKKMCTRD
SEQ ID 13:(con't)     CGGNQ--NRFESLEECKKMCTRD
SEQ ID 14: (con't.)   CGGNQ--NRFESLEECKKMCTRD
SEQ ID 15:(con't)     CGGNQ--NRFESLEECKKMCTRD
SEQ ID 16:(con't)     CGGNQ--NRFESLEECKKMCTRD
SEQ ID 17:(con't.)    CGGNQ--NRFESLEECKKMCTRD
SEQ ID 18:(con't.)    CGGNQ--NRFESLEECKKMCTRD
SEQ ID 19:(con't.)    CGGNQ--NRFESLEECKKMCTRD
SEQ ID 20:(con't.)    CGGNQ--NRFESLEECKKMCTRD
SEQ ID 21:(con't.)    CGGNQ--NRFESLEECKKMCTRD
SEQ ID 22:(con't.)    CGGNQ--NRFESLEECKKMCTRD
```

METHODS FOR PRESERVING ORGANS AND TISSUES

RELATED APPLICATION

This application is a continuation (and claims the benefit of priority under 35 USC 120) of U.S. application Ser. No. 11/621,246, filed Jan. 9, 2007, which is a divisional (and claims the benefit of priority under 35 USC 120) of U.S. application Ser. No. 10/456,981, filed Jun. 6, 2003, now U.S. Pat. No. 7,166,576, which claims the benefit of U.S. Provisional application Ser. No. 60/407,004, filed Aug. 28, 2002. The disclosure of the prior applications are considered part of (and is incorporated by reference in) the disclosure of this application.

BACKGROUND OF THE INVENTION

Preservation of the viability of donor organs is an important goal for organ transplantation. Typically the organ to be transplanted must be stored and shipped to the prospective recipient. The ability to prolong the cellular viability of the organ during storage and transportation is very important to the success of the transplant operation. Preservative solutions play an important role in the longevity of the organ. Solutions for organ preservation include those described by Berdyaev et al., U.S. Pat. No. 5,432,053; Belzer et al., U.S. Pat. Nos. 4,798,824, 4,879,283, and 4,873,230; Taylor, U.S. Pat. No. 5,405,742; Dohi et al., U.S. Pat. No. 5,565,317; Stern et al., U.S. Pat. Nos. 5,370,989 and 5,552,267, the contents of which are incorporated herein by reference in their entirety. However, a need exists for improved methods and solutions for organ preservation. Proteases are involved in a broad range of biological pathways. In particular, serine proteases such as kallikrein, plasmin, elastase, urokinase plasminogen activator, thrombin, human lipoprotein-associated coagulation inhibitor, and coagulation factors such as factors VIIa, IXa, Xa, XIa, and XIIa have been implicated in pathways affecting blood flow, e.g., general and focal ischemia, tumor invasion, fibrinolysis, perioperative blood loss, and inflammation. Inhibitors of specific serine proteases, therefore, have received attention as potential drug targets for various ischemic maladies.

One such inhibitor, aprotinin (also called bovine pancreatic trypsin inhibitor or BPTI), obtained from bovine lung, has been approved in the United States for prophylactic use in reducing perioperative blood loss and the need for transfusion in patients undergoing CPB, e.g., in the course of a coronary artery bypass grafting procedure. Aprotinin is commercially available under the trade name TRASYLOL® (Bayer Corporation Pharmaceutical Division, West Haven, Conn.) and was previously approved for use to treat pancreatitis. The effectiveness of aprotinin is associated with its relatively non-specific abilities to inhibit a variety of serine proteases, including plasma kallikrein, and plasmin. These proteases are important in a number of pathways of the contact activation system (CAS).

CAS is initially activated when whole blood contacts the surface of foreign substrates (e.g., kaolin, glass, dextran sulfate, or damaged bone surfaces). Kallikrein, a serine protease, is a plasma enzyme that initiates the CAS cascade leading to activation of neutrophils, plasmin, coagulation, and various kinins. Kallikrein is secreted as a zymogen (pre-kallikrein) that circulates as an inactive molecule until activated by a proteolytic event early in the contact activation cascade. However, the use of specific kallikrein inhibitors for organ preservation has not been successfully demonstrated.

SUMMARY OF THE INVENTION

This invention is based on the discovery of peptides that inhibit serine proteases, such as, for example, kallikrein, which can successfully be employed to preserve an organ pending transplant. More specifically, the invention provides methods of using kallikrein inhibitors in a method for preserving an organ or tissue and compositions for such use. The invention also relates to methods for reducing, inhibiting or preventing reperfusion injury or damage in an organ or tissue that has been removed from its host and compositions for such use. Preferred kallikrein peptides include those described in U.S. Pat. Nos. 6,333,402 and 6,057,287 to Markland et al., the contents of which are incorporated herein by reference in their entirety.

In a particularly preferred embodiment, the invention is directed to compositions comprising a polypeptide comprising the amino acid sequence:

```
                                            (SEQ ID NO: 1)
Xaa1 Xaa2 Xaa3 Xaa4 Cys Xaa6 Xaa7 Xaa8 Xaa9 Xaa10

Xaa11 Gly Xaa13 Cys Xaa15 Xaa16 Xaa17 Xaa18 Xaa19

Xaa20 Xaa21 Xaa22 Xaa23 Xaa24 Xaa25 Xaa26 Xaa27

Xaa28 Xaa29 Cys Xaa31 Xaa32 Phe Xaa34 Xaa35 Gly

Gly Cys Xaa39 Xaa40 Xaa41 Xaa42 Xaa43 Xaa44 Xaa45

Xaa46 Xaa47 Xaa48 Xaa49 Xaa50 Cys Xaa52 Xaa53

Xaa54 Cys Xaa56 Xaa57 Xaa58,
``` wherein Xaa1, Xaa2, Xaa3, Xaa4, Xaa56, Xaa57 or Xaa58 are each individually an amino acid or absent; Xaa6, Xaa7, Xaa8, Xaa9, Xaa20, Xaa24, Xaa25, Xaa26, Xaa27, Xaa28, Xaa29, Xaa41, Xaa42, Xaa44, Xaa46, Xaa47, Xaa48, Xaa49, Xaa50, Xaa52, Xaa53 and Xaa54 can be any amino acid; Xaa10 is an amino acid selected from the group consisting of: Asp and Glu; Xaa11 is an amino acid selected from the group consisting of: Asp, Gly, Ser, Val, Asn, Ile, Ala and Thr; Xaa13 is an amino acid selected from the group consisting of: Arg, His, Pro, Asn, Ser, Thr, Ala, Gly, Lys and Gln; Xaa15 is an amino acid selected from the group consisting of: Arg, Lys, Ala, Ser, Gly, Met, Asn and Gln; Xaa16 is an amino acid selected from the group consisting of: Ala, Gly, Ser, Asp and Asn; Xaa17 is an amino acid selected from the group consisting of: Ala, Asn, Ser, Ile, Gly, Val, Gln and Thr; Xaa18 is an amino acid selected from the group consisting of: His, Leu, Gln and Ala; Xaa19 is an amino acid selected from the group consisting of: Pro, Gln, Leu, Asn and Ile; Xaa21 is an amino acid selected from the group consisting of: Trp, Phe, Tyr, His and Ile; Xaa22 is an amino acid selected from the group consisting of: Tyr and Phe; Xaa23 is an amino acid selected from the group consisting of: Tyr and Phe; Xaa31 is an amino acid selected from the group consisting of: Glu, Asp, Gln, Asn, Ser, Ala, Val, Leu, Ile and Thr; Xaa32 is an amino acid selected from the group consisting of: Glu, Gln, Asp Asn, Pro, Thr, Leu, Ser, Ala, Gly and Val; Xaa34 is an amino acid selected from the group consisting of: Thr, Ile, Ser, Val, Ala, Asn, Gly and Leu; Xaa35 is an amino acid selected from the group consisting of: Tyr, Trp and Phe; Xaa39 is an amino acid selected from the group consisting of: Glu, Gly, Ala, Ser and Asp; Xaa40 is an amino acid selected from the group consisting of: Gly and Ala; Xaa43 is an amino acid selected from the group consisting of: Asn and Gly; Xaa45 is an amino acid selected from the group consisting of: Phe and Tyr; and wherein said polypeptide inhibits kallikrein, and methods of using such compositions.

In a particular embodiment, specific amino acid positions can be the following: Xaa6 can be Ala, Xaa7 can be Phe, Xaa8 can be Lys, Xaa9 can be Ala, Xaa10 can be Asp, Xaa11 can be Asp, Xaa13 can be Pro, Xaa15 can be Arg, Xaa16 can be Ala, Xaa17 can be Ala, Xaa18 can be His, Xaa19 can be Pro, Xaa20 can be Arg, Xaa24 can be Asn, Xaa25 can be Ile, Xaa26 can be Phe, Xaa27 can be Thr, Xaa28 can be Arg, Xaa29 can be Gln, Xaa31 can be Glu, Xaa32 can be Glu, Xaa34 can be Ile, Xaa35 can be Tyr, Xaa39 can be Glu, Xaa41 can be Asn, Xaa42 can be Arg, Xaa44 can be Arg, Xaa46 can be Glu, Xaa47 can be Ser, Xaa48 can be Leu, Xaa49 can be Glu, and/or Xaa50 can be Glu; any of these specific amino acids at these positions can occur individually or in combination with one or more of the amino acids at one or more position otherwise described.

In a particular embodiment, the present invention is directed to a composition comprising a polypeptide as described in SEQ ID NO:1, such that two or more of the following amino acid positions are defined as follows: Xaa10 can be Asp; Xaa11 can be Asp; Xaa13 can be Pro; Xaa15 can be Arg; Xaa16 can be Ala; Xaa17 can be Ala; Xaa18 can be His; Xaa19 can be Pro; Xaa21 can be Trp; Xaa22 can be Phe; Xaa23 can be Phe; Xaa31 can be Glu; Xaa32 can be Glu; Xaa34 can be Ile; Xaa35 can be Tyr; Xaa39 can be Glu; Xaa40 can be Gly; Xaa43 can be Asn; and Xaa45 can be Phe, and methods of using such compositions. In another embodiment, five or more of the following of the following amino acid positions are defined as follows: Xaa10 can be Asp; Xaa11 can be Asp; Xaa13 can be Pro; Xaa15 can be Arg; Xaa16 can be Ala; Xaa17 can be Ala; Xaa18 can be His; Xaa19 can be Pro; Xaa21 can be Trp; Xaa22 can be Phe; Xaa23 can be Phe; Xaa31 can be Glu; Xaa32 can be Glu; Xaa34 can be Ile; Xaa35 can be Tyr; Xaa39 can be Glu; Xaa40 can be Gly; Xaa43 can be Asn; and Xaa45 can be Phe. In another embodiment, 10 or more of the amino acids are defined as follows: Xaa10 can be Asp; Xaa11 can be Asp; Xaa13 can be Pro; Xaa15 can be Arg; Xaa16 can be Ala; Xaa17 can be Ala; Xaa18 can be His; Xaa19 can be Pro; Xaa21 can be Trp; Xaa22 can be Phe; Xaa23 can be Phe; Xaa31 can be Glu; Xaa32 can be Glu; Xaa34 can be Ile; Xaa35 can be Tyr; Xaa39 can be Glu; Xaa40 can be Gly; Xaa43 can be Asn; and Xaa45 can be Phe. In yet another embodiment, 15 or more of the amino acids are defined as follows: Xaa10 can be Asp; Xaa11 can be Asp; Xaa13 can be Pro; Xaa15 can be Arg; Xaa16 can be Ala; Xaa17 can be Ala; Xaa18 can be His; Xaa19 can be Pro; Xaa21 can be Trp; Xaa22 can be Phe; Xaa23 can be Phe; Xaa31 can be Glu; Xaa32 can be Glu; Xaa34 can be Ile; Xaa35 can be Tyr; Xaa39 can be Glu; Xaa40 can be Gly; Xaa43 can be Asn; and Xaa45 can be Phe.

In a particular embodiment, the invention is directed to a composition comprising a polypeptide as defined by SEQ ID NO:1, such that, if present, Xaa3 is Ser, Xaa2 is His, Xaa1 is Met, Xaa56 is Thr, Xaa57 is Arg, and/or Xaa58 is Asp, and methods of using such compositions.

In another embodiment, the invention is directed to a composition comprising a polypeptide comprising the amino acid sequence:
Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (SEQ ID NO:2), and methods of using such compositions.

In a particular embodiment, the present invention is directed to a composition comprising a kallikrein binding polypeptide of 53-60 amino acids comprising a Kunitz domain, wherein the Kunitz domain comprises the potential for disulfide bonds between cysteines at positions 5 and 55; 14 and 38; and 30 and 51 (according to amino acid positions corresponding to bovine pancreatic trypsin inhibitor (BPTI)), and further comprising:
  amino acid number 13 selected from His and Pro;
  amino acid number 16 selected from Ala and Gly;
  amino acid number 17 selected from Ala, Asn, and Ser;
  amino acid number 18 selected from His and Leu; and
  amino acid number 19 selected from Gln, Leu, and Pro (SEQ ID NO:23).

In a particular embodiment, the present invention is directed to a composition comprising a kallikrein binding polypeptide of 53-60 amino acids comprising a Kunitz domain, wherein the Kunitz domain comprises the potential for disulfide bonds between cysteines at positions 5 and 55; 14 and 38; and 30 and 51 (according to amino acid positions corresponding to bovine pancreatic trypsin inhibitor (BPTI)), and further comprising:
  amino acid number 13 selected from His and Pro;
  amino acid number 15 selected from Lys and Arg;
  amino acid number 16 selected from Ala and Gly;
  amino acid number 17 selected from Ala, Asn, and Ser;
  amino acid number 18 selected from His and Leu; and
  amino acid number 19 selected from Gln, Leu, and Pro,
  amino acid number 31 is Glu;
  amino acid number 32 selected from Glu and Gln;
  amino acid number 34 selected from Ser, Thr, and Ile; and
  amino acid number 39 selected from Gly, Glu, and Ala (SEQ ID NO:24).

In a particular embodiment, the present invention is directed to a composition comprising a kallikrein binding polypeptide of 53-60 amino acids comprising a Kunitz domain, wherein the Kunitz domain comprises a cysteine at each of positions 5 and 55; 14 and 38; and 30 and 51 (according to amino acid positions corresponding to bovine pancreatic trypsin inhibitor (BPTI)), and further comprising:
  amino acid number 13 selected from His and Pro;
  amino acid number 15 selected from Lys and Arg;
  amino acid number 16 selected from Ala and Gly;
  amino acid number 17 selected from Ala, Asn, and Ser;
  amino acid number 18 selected from His and Leu; and
  amino acid number 19 selected from Gln, Leu, and Pro,
  amino acid number 31 is Glu;
  amino acid number 32 selected from Glu and Gln;
  amino acid number 34 selected from Ser, Thr, and Ile; and
  amino acid number 39 selected from Gly, Glu, and Ala (SEQ ID NO:24).

In a particular embodiment, the Kunitz domain is selected from the group consisting of:
  KKII/3 #1 (SEQ ID NO:24)
  KKII/3 #2 (SEQ ID NO:25)
  KKII/3 #3 (SEQ ID NO:26)
  KKII/3 #4 (SEQ ID NO:27)
  KKII/3 #5 (SEQ ID NO:28)
  KKII/3 #6 (SEQ ID NO:29)
  KKII/3 #7 (SEQ ID NO:30)
  KKII/3 #8 (SEQ ID NO:31)
  KKII/3 #9 (SEQ ID NO:32) and
  KKII/3 #10 (SEQ ID NO:33)
  as described in Table 1.

Each of the compositions described herein can be used in the methods of the invention. Further, the compounds described herein can be used in the manufacture of a medicament or composition for the indications or methods described herein.

BRIEF DESCRIPTION OF THE DRAWINGS

FIG. 2 shows a portion of a DNA and corresponding deduced amino acid for a kallikrein inhibitor ("KI") polypeptide of the invention in plasmid pPIC-K503. The inserted DNA encodes the mata prepro signal peptide of *Saccharomyces cerevisiae* (underlined) fused in frame to the amino terminus of the PEP-1 KI polypeptide having the amino acid sequence enclosed by the boxed area. The amino acid sequence of the PEP-1 KI polypeptide shown in the boxed region is SEQ ID NO:2, and the corresponding nucleotide coding sequence of the KI polypeptide is SEQ ID NO:3. The dashed arrows indicate the location and direction of two PCR primer sequences in AOX regions that were used to produce sequencing templates. DNA sequence for the entire nucleotide sequence of the figure comprises the structural coding sequence for the fusion protein and is designated SEQ ID NO:35. The double underlined portion of the sequence indicates a diagnostic probe sequence. BstBI and EcoRI indicate locations of their respective palindromic, hexameric, restriction endonuclease sites in the sequence. Asterisks denote translational stop codons.

FIG. 3 shows an alignment of amino acid sequences of the preferred embodiments of the invention.

DETAILED DESCRIPTION OF THE INVENTION

Figure 1:
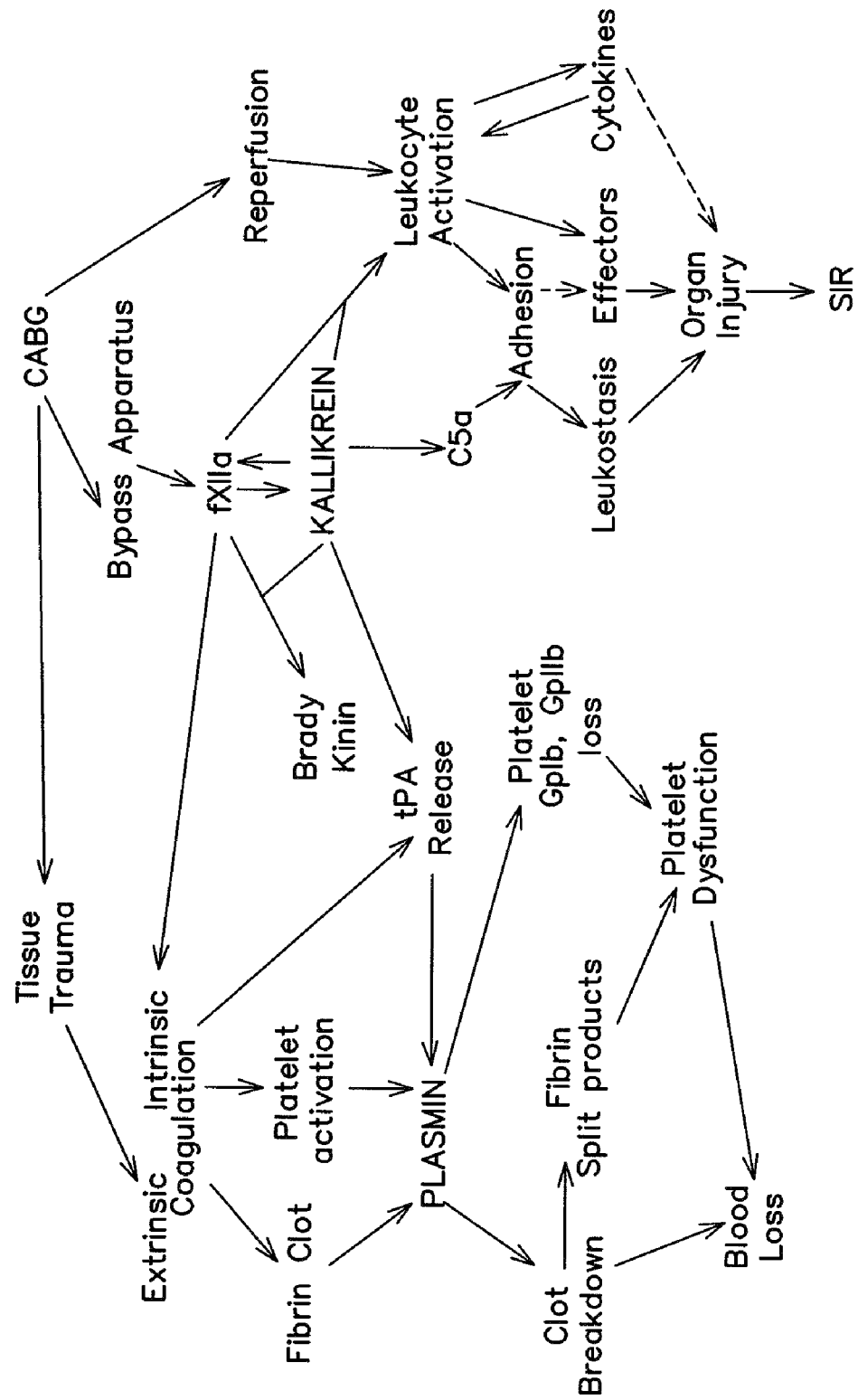
FIG. 1 is a simplified diagram of major multiple pathways and related events involved in the contact activation system and systemic inflammatory response (SIR) that may arise in a patient subjected to soft and bone tissue trauma such as that associated with a coronary artery bypass grafting (CABG) procedure, especially when the CABG procedure involves extra-corporeal blood circulation, such as cardiopulmonary bypass (CPB; Bypass Apparatus). Arrows indicate activation from one component or event to another component or event in the cascade. Arrows in both directions indicate activating effects of components or events in both directions. Broken arrows indicate likely participation of one component or event in the activation of another component or event. Abbreviations are as follows: "tPA"=tissue plasminogen activator; "C5a"=a protein component of the complement system; "fXIIa"=activator protein of pre-kallikrein to form active kallikrein; "Extrinsic"=extrinsic coagulation system; "Intrinsic"=intrinsic coagulation system.

A description of preferred embodiments of the invention follows.

The invention is based on the discovery of kallikrein inhibitor (KI) polypeptides that inhibit plasma kallikrein with a specificity that permits their use in improved methods of preserving organs and tissues, such as pending a transplantation, and to corresponding methods. The invention also relates to reducing, inhibiting or preventing reperfusion injury or damage in an organ or tissue that has been removed from its host and compositions therefor.

Polypeptides Useful in the Invention

KI polypeptides useful in the invention comprise Kunitz domain polypeptides. In one embodiment these Kunitz domains are variant forms comprising the looped structure of Kunitz domain 1 of human lipoprotein-associated coagulation inhibitor (LACI) protein. LACI contains three internal, well-defined, peptide loop structures that are paradigm Kunitz domains (Girard, T. et al., 1989. *Nature,* 338:518-520). The three Kunitz domains of LACI confer the ability to bind and inhibit kallikrein, although not with exceptional affinity. Variants of Kunitz domain 1 of LACI described herein have been screened, isolated and bind kallikrein with enhanced affinity and specificity (see, for example, U.S. Pat. Nos. 5,795,865 and 6,057,287, incorporated herein by reference). An example of a preferred polypeptide useful in the invention has the amino acid sequence defined by amino acids 3-60 of SEQ ID NO:2.

Kallikrein binding polypeptides can be used to target therapeutic or diagnostic molecules to kallikrein in, for example, organ tissue, cells, or whole organisms. Such methods of targeted delivery for therapeutic or diagnostic purposes would be known to one of skill in the art. For example, targeted kallikrein binding polypeptides could be used by one of skill in the art to identify an organ that has been damaged by the effects of kallikrein, or kallikrein can be targeted for the effects of a particular therapeutic agent using kallikrein binding polypeptides of the invention.

Every polypeptide useful in the invention binds kallikrein. In preferred embodiments, the polypeptides are kallikrein inhibitors (KI) as determined using kallikrein binding and inhibition assays known in the art. The enhanced affinity and specificity for kallikrein of the variant Kunitz domain polypeptides described herein provides the basis for their use in CPB and especially CABG surgical procedures to prevent or reduce perioperative blood loss and/or SIR in patients undergoing such procedures. The KI polypeptides used in the invention can have or comprise the amino acid sequence of a variant Kunitz domain polypeptide originally isolated by screening phage display libraries for the ability to bind kallikrein.

KI polypeptides useful in the methods and compositions of the invention comprise a Kunitz domain polypeptide comprising the amino acid sequence:

```
                                              (SEQ ID NO: 1)
Xaa1 Xaa2 Xaa3 Xaa4 Cys Xaa6 Xaa7 Xaa8 Xaa9 Xaa10

Xaa11 Gly Xaa13 Cys Xaa15 Xaa16 Xaa17 Xaa18 Xaa19

Xaa20 Xaa21 Xaa22 Xaa23 Xaa24 Xaa25 Xaa26 Xaa27

Xaa28 Xaa29 Cys Xaa31 Xaa32 Phe Xaa34 Xaa35 Gly

Gly Cys Xaa39 Xaa40 Xaa41 Xaa42 Xaa43 Xaa44 Xaa45

Xaa46 Xaa47 Xaa48 Xaa49 Xaa50 Cys Xaa52 Xaa53

Xaa54 Cys Xaa56 Xaa57 Xaa58
```

"Xaa" refers to a position in a peptide chain that can be any of a number of different amino acids. For example, for the KI peptides described herein, Xaa10 can be Asp or Glu; Xaa11 can be Asp, Gly, Ser, Val, Asn, Ile, Ala or Thr; Xaa13 can be Pro, Arg, His, Asn, Ser, Thr, Ala, Gly, Lys or Gln; Xaa15 can be Arg, Lys, Ala, Ser, Gly, Met, Asn or Gln; Xaa16 can be Ala, Gly, Ser, Asp or Asn; Xaa17 can be Ala, Asn, Ser, Ile, Gly, Val, Gln or Thr; Xaa18 can be His, Leu, Gln or Ala; Xaa19 can be Pro, Gln, Leu, Asn or Ile; Xaa21 can be Trp, Phe, Tyr, His or Ile; Xaa31 can be Glu, Asp, Gln, Asn, Ser, Ala, Val, Leu, Ile or Thr; Xaa32 can be Glu, Gln, Asp Asn, Pro, Thr, Leu, Ser, Ala, Gly or Val; Xaa34 can be Ile, Thr, Ser, Val, Ala, Asn, Gly or Leu; Xaa35 can be Tyr, Trp or Phe; Xaa39 can be Glu, Gly, Ala, Ser or Asp. Amino acids Xaa6, Xaa7, Xaa8, Xaa9, Xaa20, Xaa24, Xaa25, Xaa26, Xaa27, Xaa28, Xaa29, Xaa41, Xaa42, Xaa44, Xaa46, Xaa47, Xaa48, Xaa49, Xaa50, Xaa52, Xaa53 and Xaa54 can be any amino acid. Additionally, each of the first four and at last three amino acids of SEQ ID NO:1 can optionally be present or absent and can be any amino acid, if present.

Peptides defined according to SEQ ID NO:1 form a set of polypeptides that bind to and inhibit kallikrein. The diversity of the KI's is increased as the number of variable positions in the peptide sequence is increased or as the number of amino acids possible at a variable position increases. For example, in a preferred embodiment of the invention, a KI polypeptide useful in the methods and compositions of the invention has the following variable positions: Xaa11 can be Asp, Gly, Ser or Val; Xaa13 can be Pro, Arg, His or Asn; Xaa15 can be Arg or Lys; Xaa16 can be Ala or Gly; Xaa17 can be Ala, Asn, Ser or Ile; Xaa18 can be His, Leu or Gln; Xaa19 can be Pro, Gln or Leu; Xaa21 can be Trp or Phe; Xaa31 is Glu; Xaa32 can be Glu or Gln; Xaa34 can be Ile, Thr or Ser; Xaa35 is Tyr; and Xaa39 can be Glu, Gly or Ala.

A more specific embodiment of the claimed invention is defined by the following amino acids at variable positions: Xaa10 is Asp; Xaa11 is Asp; Xaa13 can be Pro or Arg; Xaa15 is Arg; Xaa16 can be Ala or Gly; Xaa17 is Ala; Xaa18 is His; Xaa19 is Pro; Xaa21 is Trp; Xaa31 is Glu; Xaa32 is Glu; Xaa34 can be Ile or Ser; Xaa35 is Tyr; and Xaa39 is Gly.

Also encompassed within the scope of the invention are peptides that comprise portions of the polypeptides described herein. For example, polypeptides could comprise binding domains for specific kallikrein epitopes. Such fragments of the polypeptides described herein would also be encompassed.

KI polypeptides useful in the methods and compositions described herein comprise a Kunitz domain. A subset of the sequences encompassed by SEQ ID NO:1 are described by the following (where not indicated, "Xaa" refers to the same set of amino acids that are allowed for SEQ ID NO:1):

```
                                                (SEQ ID NO: 36)
Met His Ser Phe Cys Ala Phe Lys Ala Xaa10 Xaa11

Gly Xaa13 Cys Xaa15 Xaa16 Xaa17 Xaa18 Xaa19

Arg Xaa21 Phe Phe Asn Ile Phe Thr Arg Gln Cys

Xaa31 Xaa32 Phe Xaa34 Xaa35 Gly Gly Cys Xaa39

Gly Asn Gln Asn Arg Phe Glu Ser Leu Glu Glu Cys

Lys Lys Met Cys Thr Arg Asp.
```

Specific and particular examples of KI peptides useful in the invention described herein are as follows:

```
                                        (amino acids 3-60 of SEQ ID NO: 2)
Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp, (SEQ ID NO: 4)
Met His Ser Phe Cys Ala Phe Lys Ala Asp Asp Gly Pro Cys Lys Ala Asn His Leu Arg Phe Phe Phe Asn Ile Phe Thr Arg Gln Cys Glu Glu Phe Ser Tyr Gly Gly Cys Gly Gly Asn Gln Asn Arg Phe Glu Ser Leu Glu Glu Cys Lys Lys Met Cys Thr Arg Asp, (SEQ ID NO: 5)
Met His Ser Phe Cys Ala Phe Lys Ala Asp Asp Gly His Cys Lys Ala Asn His Gln Arg Phe Phe Phe Asn Ile Phe Thr Arg Gln Cys Glu Glu Phe Thr Tyr Gly Gly Cys Gly Gly Asn Gln Asn Arg Phe Glu Ser Leu Glu Glu Cys Lys Lys Met Cys Thr Arg Asp, (SEQ ID NO: 6)
Met His Ser Phe Cys Ala Phe Lys Ala Asp Asp Gly His Cys Lys Ala Asn His Gln Arg Phe Phe Phe Asn Ile Phe Thr Arg Gln Cys Glu Gln Phe Thr Tyr Gly Gly Cys Ala Gly Asn Gln Asn Arg Phe Glu Ser Leu Glu Glu Cys Lys Lys Met Cys Thr Arg Asp, (SEQ ID NO: 7)
Met His Ser Phe Cys Ala Phe Lys Ala Asp Asp Gly His Cys Lys Ala Ser Leu Pro Arg Phe Phe Phe Asn Ile Phe Thr Arg Gln Cys Glu Glu Phe Ile Tyr Gly Gly Cys Gly Gly Asn Gln Asn Arg Phe Glu Ser Leu Glu Glu Cys Lys Lys Met Cys Thr Arg Asp, (SEQ ID NO: 8)
Met His Ser Phe Cys Ala Phe Lys Ala Asp Asp Gly His Cys Lys Ala Asn His Gln Arg Phe Phe Phe Asn Ile Phe Thr Arg Gln Cys Glu Glu Phe Ser Tyr Gly Gly Cys Gly Gly Asn Gln Asn Arg Phe Glu Ser Leu Glu Glu Cys Lys Lys Met Cys Thr Arg Asp, (SEQ ID NO: 9)
Met His Ser Phe Cys Ala Phe Lys Ala Asp Asp Gly His Cys Lys Gly Ala His Leu Arg Phe Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp,
```

-continued (SEQ ID NO: 10)
Met His Ser Phe Cys Ala Phe Lys Ala Asp Asp Gly Arg Cys Lys Gly Ala His Leu Arg Phe
Phe Phe Asn Ile Phe Thr Arg Gln Cys Glu Glu Phe Ile Tyr Gly Gly Cys Glu Gly Asn Gln Asn
Arg Phe Glu Ser Leu Glu Glu Cys Lys Lys Met Cys Thr Arg Asp, (SEQ ID NO: 11)
Met His Ser Phe Cys Ala Phe Lys Ala Asp Gly Gly Arg Cys Arg Gly Ala His Pro Arg Trp
Phe Phe Asn Ile Phe Thr Arg Gln Cys Glu Glu Phe Ser Tyr Gly Gly Cys Gly Gly Asn Gln
Asn Arg Phe Glu Ser Leu Glu Glu Cys Lys Lys Met Cys Thr Arg Asp, (SEQ ID NO: 12)
Met His Ser Phe Cys Ala Phe Lys Ala Asp Asp Gly Pro Cys Arg Ala Ala His Pro Arg Trp
Phe Phe Asn Ile Phe Thr Arg Gln Cys Glu Glu Phe Ser Tyr Gly Gly Cys Gly Gly Asn Gln
Asn Arg Phe Glu Ser Leu Glu Glu Cys Lys Lys Met Cys Thr Arg Asp, (SEQ ID NO: 13)
Met His Ser Phe Cys Ala Phe Lys Ala Asp Val Gly Arg Cys Arg Gly Ala His Pro Arg Trp
Phe Phe Asn Ile Phe Thr Arg Gln Cys Glu Glu Phe Ser Tyr Gly Gly Cys Gly Gly Asn Gln
Asn Arg Phe Glu Ser Leu Glu Glu Cys Lys Lys Met Cys Thr Arg Asp, (SEQ ID NO: 14)
Met His Ser Phe Cys Ala Phe Lys Ala Asp Val Gly Arg Cys Arg Gly Ala Gln Pro Arg Phe
Phe Phe Asn Ile Phe Thr Arg Gln Cys Glu Glu Phe Ser Tyr Gly Gly Cys Gly Gly Asn Gln
Asn Arg Phe Glu Ser Leu Glu Glu Cys Lys Lys Met Cys Thr Arg Asp, (SEQ ID NO: 15)
Met His Ser Phe Cys Ala Phe Lys Ala Asp Asp Gly Ser Cys Arg Ala Ala His Leu Arg Trp
Phe Phe Asn Ile Phe Thr Arg Gln Cys Glu Glu Phe Ser Tyr Gly Gly Cys Gly Gly Asn Gln
Asn Arg Phe Glu Ser Leu Glu Glu Cys Lys Lys Met Cys Thr Arg Asp, (SEQ ID NO: 16)
Met His Ser Phe Cys Ala Phe Lys Ala Glu Gly Gly Ser Cys Arg Ala Ala His Gln Arg Trp
Phe Phe Asn Ile Phe Thr Arg Gln Cys Glu Glu Phe Ser Tyr Gly Gly Cys Gly Gly Asn Gln
Asn Arg Phe Glu Ser Leu Glu Glu Cys Lys Lys Met Cys Thr Arg Asp, (SEQ ID NO: 17)
Met His Ser Phe Cys Ala Phe Lys Ala Asp Asp Gly Pro Cys Arg Gly Ala His Leu Arg Phe
Phe Phe Asn Ile Phe Thr Arg Gln Cys Glu Glu Phe Ser Tyr Gly Gly Cys Gly Gly Asn Gln
Asn Arg Phe Glu Ser Leu Glu Glu Cys Lys Lys Met Cys Thr Arg Asp, (SEQ ID NO: 18)
Met His Ser Phe Cys Ala Phe Lys Ala Asp Asp Gly His Cys Arg Gly Ala Leu Pro Arg Trp
Phe Phe Asn Ile Phe Thr Arg Gln Cys Glu Glu Phe Ser Tyr Gly Gly Cys Gly Gly Asn Gln
Asn Arg Phe Glu Ser Leu Glu Glu Cys Lys Lys Met Cys Thr Arg Asp, (SEQ ID NO: 19)
Met His Ser Phe Cys Ala Phe Lys Ala Asp Ser Gly Asn Cys Arg Gly Asn Leu Pro Arg Phe
Phe Phe Asn Ile Phe Thr Arg Gln Cys Glu Glu Phe Ser Tyr Gly Gly Cys Gly Gly Asn Gln
Asn Arg Phe Glu Ser Leu Glu Glu Cys Lys Lys Met Cys Thr Arg Asp, (SEQ ID NO: 20)
Met His Ser Phe Cys Ala Phe Lys Ala Asp Ser Gly Arg Cys Arg Gly Asn His Gln Arg Phe
Phe Phe Asn Ile Phe Thr Arg Gln Cys Glu Glu Phe Ser Tyr Gly Gly Cys Gly Gly Asn Gln
Asn Arg Phe Glu Ser Leu Glu Glu Cys Lys Lys Met Cys Thr Arg Asp,

```
                                                              (SEQ ID NO: 21)
Met His Ser Phe Cys Ala Phe Lys Ala Asp Gly Gly Arg Cys Arg Ala Ile Gln Pro Arg Trp Phe

Phe Asn Ile Phe Thr Arg Gln Cys Glu Glu Phe Ser Tyr Gly Gly Cys Gly Gly Asn Gln Asn

Arg Phe Glu Ser Leu Glu Glu Cys Lys Lys Met Cys Thr Arg Asp, (SEQ ID NO: 22)
Met His Ser Phe Cys Ala Phe Lys Ala Asp Asp Gly Arg Cys Arg Gly Ala His Pro Arg Trp

Phe Phe Asn Ile Phe Thr Arg Gln Cys Glu Glu Phe Ser Tyr Gly Gly Cys Gly Gly Asn Gln

Asn Arg Phe Glu Ser Leu Glu Glu Cys Lys Lys Met Cys Thr Arg Asp.
```

FIG. 3 provides an amino acid sequence alignment of these sequences.

Other KI polypeptides useful in the present invention include:

```
                                                              (SEQ ID NO: 23)
Arg Pro Asp Phe Cys Leu Glu Pro Pro Tyr Thr Gly Pro Cys Lys Ala Arg Ile Ile Arg Tyr Phe

Tyr Asn Ala Lys Ala Gly Leu Cys Gln Thr Phe Val Tyr Gly Gly Cys Arg Ala Lys Arg Asn

Asn Phe Lys Ser Ala Glu Asp Cys Met Arg Thr Cys Gly Gly Ala, (SEQ ID NO: 24)
Met His Ser Phe Cys Ala Phe Lys Ala Asp Asp Gly His Cys Lys Ala Ser Leu Pro Arg Phe

Phe Phe Asn Ile Phe Thr Arg Gln Cys Glu Glu Phe Ile Tyr Gly Gly Cys Glu Gly Asn Gln Asn

Arg Phe Glu Ser Leu Glu Glu Cys Lys Lys Met Cys Thr Arg Asp, (SEQ ID NO: 25)
Met His Ser Phe Cys Ala Phe Lys Ala Asp Asp Gly Pro Cys Lys Ala Asn His Leu Arg Phe

Phe Phe Asn Ile Phe Thr Arg Gln Cys Glu Glu Phe Ser Tyr Gly Gly Cys Gly Gly Asn Gln

Asn Arg Phe Glu Ser Leu Glu Glu Cys Lys Lys Met Cys Thr Arg Asp, (SEQ ID NO: 26)
Met His Ser Phe Cys Ala Phe Lys Ala Asp Asp Gly His Cys Lys Ala Asn His Gln Arg Phe

Phe Phe Asn Ile Phe Thr Arg Gln Cys Glu Glu Phe Thr Tyr Gly Gly Cys Gly Gly Asn Gln

Asn Arg Phe Glu Ser Leu Glu Glu Cys Lys Lys Met Cys Thr Arg Asp, (SEQ ID NO: 27)
Met His Ser Phe Cys Ala Phe Lys Ala Asp Asp Gly His Cys Lys Ala Asn His Gln Arg Phe

Phe Phe Asn Ile Phe Thr Arg Gln Cys Glu Gln Phe Thr Tyr Gly Gly Cys Ala Gly Asn Gln

Asn Arg Phe Glu Ser Leu Glu Glu Cys Lys Lys Met Cys Thr Arg Asp, (SEQ ID NO: 28)
Met His Ser Phe Cys Ala Phe Lys Ala Asp Asp Gly His Cys Lys Ala Ser Leu Pro Arg Phe

Phe Phe Asn Ile Phe Thr Arg Gln Cys Glu Glu Phe Ile Tyr Gly Gly Cys Gly Gly Asn Gln Asn

Arg Phe Glu Ser Leu Glu Glu Cys Lys Lys Met Cys Thr Arg Asp, (SEQ ID NO: 29)
Met His Ser Phe Cys Ala Phe Lys Ala Asp Asp Gly His Cys Lys Ala Asn His Gln Arg Phe

Phe Phe Asn Ile Phe Thr Arg Gln Cys Glu Glu Phe Ser Tyr Gly Gly Cys Gly Gly Asn Gln

Asn Arg Phe Glu Ser Leu Glu Glu Cys Lys Lys Met Cys Thr Arg Asp, (SEQ ID NO: 30)
Met His Ser Phe Cys Ala Phe Lys Ala Asp Asp Gly His Cys Lys Ala Asn His Gln Arg Phe

Phe Phe Asn Ile Phe Thr Arg Gln Cys Glu Glu Phe Ser Tyr Gly Gly Cys Gly Gly Asn Gln

Asn Arg Phe Glu Ser Leu Glu Glu Cys Lys Lys Met Cys Thr Arg Asp,
```

-continued (SEQ ID NO: 31)
Met His Ser Phe Cys Ala Phe Lys Ala Asp Asp Gly His Cys Lys Ala Asn His Gln Arg Phe Phe Phe Asn Ile Phe Thr Arg Gln Cys Glu Glu Phe Ser Tyr Gly Gly Cys Gly Gly Asn Gln Asn Arg Phe Glu Ser Leu Glu Glu Cys Lys Lys Met Cys Thr Arg Asp, (SEQ ID NO: 32)
Met His Ser Phe Cys Ala Phe Lys Ala Asp Asp Gly His Cys Lys Ala Asn His Gln Arg Phe Phe Phe Asn Ile Phe Thr Arg Gln Cys Glu Glu Phe Ser Tyr Gly Gly Cys Gly Gly Asn Gln Asn Arg Phe Glu Ser Leu Glu Glu Cys Lys Lys Met Cys Thr Arg Asp, (SEQ ID NO: 33)
Met His Ser Phe Cys Ala Phe Lys Ala Asp Asp Gly His Cys Lys Gly Ala His Leu Arg Phe Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp, (SEQ ID NO: 34)
Met His Ser Phe Cys Ala Phe Lys Ala Asp Asp Gly Pro Cys Lys Ala Ile Met Lys Arg Phe Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp.

These sequences are summarized in the following Table 1.

TABLE 1

Amino acid sequences of LACI(K1) variants selected for binding to human plasma kallikrein.

| | 13 | 16 | 17 | 18 | 19 | 31 | 32 | 34 | 39(a) |
|---|---|---|---|---|---|---|---|---|---|
| KKII/3#1 (SEQ ID NO: 24) | H | A | S | L | P | E | E | I | E |
| KKII/3#2 (SEQ ID NO: 25) | P | A | N | H | L | E | E | S | G |
| KKII/3#3 (SEQ ID NO: 26) | H | A | N | H | Q | E | E | T | G |
| KKII/3#4 (SEQ ID NO: 27) | H | A | N | H | Q | E | Q | T | A |
| KKII/3#5 (SEQ ID NO: 28) | H | A | S | L | P | E | E | I | G |
| KKII/3#6 (SEQ ID NO: 29) | H | A | N | H | Q | E | E | S | G |
| KKII/3#7 (SEQ ID NO: 30) | H | A | N | H | Q | E | E | S | G |
| KKII/3#8 (SEQ ID NO: 31) | H | A | N | H | Q | E | E | S | G |
| KKII/3#9 (SEQ ID NO: 32) | H | A | N | H | Q | E | E | S | G |
| KKII/3#10 (SEQ ID NO: 33) | H | G | A | H | L | E | E | I | E |
| Consensus | H | A | N | H | Q | E | E | S/T | G |

(a)Amino acid numbers of variegated residues. LACI(K1) (LACI residues 50-107 (SEQ ID NO: 32)) is 58 amino acids long with the P1 position being residue number 15 and fixed as lysine in this instance.

The polypeptides useful in the methods and compositions described herein may be made synthetically using any standard polypeptide synthesis protocol and equipment. For example, the stepwise synthesis of a KI polypeptide described herein may be carried out by the removal of an amino (N) terminal-protecting group from an initial (i.e., carboxy-terminal) amino acid, and coupling thereto of the carboxyl end of the next amino acid in the sequence of the polypeptide. This amino acid is also suitably protected. The carboxyl group of the incoming amino acid can be activated to react with the N-terminus of the bound amino acid by formation into a reactive group such as formation into a carbodiimide, a symmetric acid anhydride, or an "active ester" group such as hydroxybenzotriazole or pentafluorophenyl esters.

Preferred solid-phase peptide synthesis methods include the BOC method, which utilizes tert-butyloxycarbonyl as the a-amino protecting group, and the FMOC method, which utilizes 9-fluorenylmethloxycarbonyl to protect the a-amino of the amino acid residues. Both methods are well known to those of skill in the art (Stewart, J. and Young, J., *Solid-Phase Peptide Synthesis* (W.H. Freeman Co., San Francisco 1989); Merrifield, J., 1963. *Am. Chem. Soc.*, 85:2149-2154; Bodanszky, M. and Bodanszky, A., *The Practice of Peptide Synthesis* (Springer-Verlag, New York 1984), the entire teachings of these references is incorporated herein by reference). If desired, additional amino- and/or carboxy-terminal amino acids may be designed into the amino acid sequence and added during polypeptide synthesis.

Alternatively, Kunitz domain polypeptides and KI polypeptides useful in the compositions and methods of the invention may be produced by recombinant methods using any of a number of cells and corresponding expression vectors, including but not limited to bacterial expression vectors, yeast expression vectors, baculovirus expression vectors, mammalian viral expression vectors, and the like. Kunitz domain polypeptides and KI polypeptides useful in the compositions and methods of the invention may also be produced transgenically using nucleic acid molecules comprising a coding sequence for a Kunitz domain or KI polypeptide described herein, wherein the nucleic acid molecule can be integrated into and expressed from the genome of a host animal using transgenic methods available in the art. In some cases, it may be necessary or advantageous to fuse the coding sequence for a Kunitz domain polypeptide or a KI polypeptide comprising the Kunitz domain to another coding sequence in an expression vector to form a fusion polypeptide that is readily expressed in a host cell. Preferably, the host cell that expresses such a fusion polypeptide also processes the fusion polypeptide to yield a Kunitz domain or KI polypeptide useful in the invention that contains only the desired amino acid sequence. Obviously, if any other amino acid(s) remain attached to the expressed Kunitz domain or KI polypeptide, such additional amino acid(s) should not diminish the kallikrein binding and/or kallikrein inhibitory activity of the Kunitz domain or KI polypeptide so as to preclude use of the polypeptide in the methods or compositions of the invention.

A preferred recombinant expression system for producing KI polypeptides useful in the methods and compositions described herein is a yeast expression vector, which permits a nucleic acid sequence encoding the amino acid sequence for a KI polypeptide or Kunitz domain polypeptide to be linked in the same reading frame with a nucleotide sequence encoding the mata prepro leader peptide sequence of *Saccharomyces cerevisiae*, which in turn is under the control of an operable yeast promoter. The resulting recombinant yeast expression plasmid may then be transformed by standard methods into the cells of an appropriate, compatible yeast host, which cells are able to express the recombinant protein from the recombinant yeast expression vector. Preferably, a host yeast cell transformed with such a recombinant expression vector is also able to process the fusion protein to provide an active KI polypeptide useful in the methods and compositions of the invention. A preferred yeast host for producing recombinant Kunitz domain polypeptides and KI polypeptides comprising such Kunitz domains is *Pichia pastoris*.

As noted above, KI polypeptides that are useful in the methods and compositions described herein may comprise a Kunitz domain polypeptide described herein. Some KI polypeptides may have an additional flanking sequence, preferably of one to six amino acids in length, at the amino and/or carboxy-terminal end, provided such additional amino acids do not significantly diminish kallikrein binding affinity or kallikrein inhibition activity so as to preclude use in the methods and compositions described herein. Such additional amino acids may be deliberately added to express a KI polypeptide in a particular recombinant host cell or may be added to provide an additional function, e.g., to provide a peptide to link the KI polypeptide to another molecule or to provide an affinity moiety that facilitates purification of the polypeptide. Preferably, the additional amino acid(s) do not include cysteine, which could interfere with the disulfide bonds of the Kunitz domain. Native examples of Kunitz domains exhibit disulfide bonds, e.g., BPTI contains disulfide bonds between cysteine residues at amino acid positions 5 and 55; 14 and 38; and 30 and 51

An example of a preferred Kunitz domain polypeptide useful in the methods and compositions of the invention has the amino acid sequence of residues 3-60 of SEQ ID NO:2. When expressed and processed in a yeast fusion protein expression system (e.g., based on the integrating expression plasmid pHIL-D2), such a Kunitz domain polypeptide retains an additional amino terminal Glu-Ala dipeptide from the fusion with the mata prepro leader peptide sequence of *S. cerevisiae*. When secreted from the yeast host cell, most of the leader peptide is processed from the fusion protein to yield a functional KI polypeptide (also referred to as "PEP-1" or "DX88") having the amino acid sequence of SEQ ID NO:2 (see boxed region in FIG. 2).

Particularly preferred KI polypeptides useful in the methods and compositions described herein have a binding affinity for kallikrein that is on the order of 1000 times higher than that of aprotinin, which is currently approved for use in CABG procedures to reduce blood loss. The surprisingly high binding affinities of such KI polypeptides described herein indicate that such KI polypeptides exhibit a high degree of specificity for kallikrein to the exclusion of other molecular targets (see Table 1, below). Thus, use of such polypeptides according to the invention reduces much of the speculation as to the possible therapeutic targets. The lower degree of specificity exhibited by, for example, aprotinin, leads to possible pleiotropic side effects and ambiguity as to its therapeutic mechanism.

The polypeptides defined by, for example, SEQ ID NO:1 contain invariant positions, e.g., positions 5, 14, 30, 51 and 55 can be Cys only. Other positions such as, for example, positions 6, 7, 8, 9, 20, 24, 25, 26, 27, 28, 29, 41, 42, 44, 46, 47, 48, 49, 50, 52, 53 and 54 can be any amino acid (including non-naturally occurring amino acids). In a particularly preferred embodiment, one or more amino acids correspond to that of a native sequence (e.g., LACI (SEQ ID NOS:32-34)). In a preferred embodiment, at least one variable position is different from that of the native sequence. In yet another preferred embodiment, the amino acids can each be individually or collectively substituted by a conservative or non-conservative amino acid substitution. Conservative amino acid substitutions replace an amino acid with another amino acid of similar chemical structure and may have no affect on protein function. Non-conservative amino acid substitutions replace an amino acid with another amino acid of dissimilar chemical structure. Examples of conserved amino acid substitutions include, for example, Asn→Asp, Arg→Lys and Ser→Thr. In a preferred embodiment, 1, 2, 3, 4, 5, 6, 7, 8, 9, 10, 11, 12, 13, 14, 15, 16, 17, 18, 19, 20 and/or 21 of these amino acids can be independently or collectively, in any combination, selected to correspond to the corresponding position of SEQ ID NO:2.

Other positions, for example, positions 10, 11, 13, 15, 16, 17, 18, 19, 21, 22, 23, 31, 32, 34, 35, 39, 40, 43 and 45, can be any of a selected set of amino acids. Thus SEQ ID NO:1 defines a set of possible sequences. Each member of this set contains, for example, a cysteine at positions 5, 14, 30, 51 and 55, and any one of a specific set of amino acids at positions 10, 11, 13, 15, 16, 17, 18, 19, 221, 22, 23, 31, 32, 34, 35, 39, 40, 43 and 45. In a preferred embodiment, 1, 2, 3, 4, 5, 6, 7, 8, 9, 10, 11, 12, 13, 14, 15, 16, 17, 18 and/or 19 of these amino acids can be independently or collectively, in any combination, selected to correspond to the corresponding position of SEQ ID NO:2. The peptide preferably has at least 80%, at least 85%, at least 90% or at least 95% identity to SEQ ID NO:2.

Methods and Compositions

The present invention is directed to methods for preserving organs and tissues comprising contacting the organ or tissue with a preservative solution comprising a kallikrein inhibitor, such as those described herein. The invention also relates to reducing, inhibiting or preventing reperfusion injury or damage in an organ or tissue that has been removed from its host comprising contacting the organ or tissue with a kallikrein inhibitor. The preservative solutions of the invention can be used to preserve and/or protect organ tissue, or whole organs, when said organs or tissue are brought into contact with the solution. A specific embodiment of the invention is for the preservation of a human heart, or human myocardial tissue. Another embodiment of the invention is for the preservation of a human lung or human lung tissue. Other organs, or parts thereof, that can be preserved according to the invention include kidney, liver, endothelial tissue, intestinal tissue, vascular tissue (e.g., an aorta graft), skin, and pancreas. The invention contemplates the use of the solutions to preserve mammalian tissue, organs or portion thereof. In addition, the solutions can be used to facilitate transplantation of organs, e.g., by perfusion of the organ or tissue during the transplantation procedure. The solution can also be used as a cardioplegia solution in cardiac surgery. Preferably, the organ or portion thereof, is maintained in the appropriate solution at all times, particularly prior to the transplant procedure.

The solutions of the invention can be used to maintain viability of the organ or tissue during storage, transplantation or other surgery. The invention includes a method of storing tissue or organs comprising contacting said tissue, organ or part thereof, with the solution of the invention, such that the in vivo and/or in vitro viability is prolonged. The solutions permit maintenance of viability of heart or lung tissue for up to 24 hours or more. Use of the solutions of the invention results in improved organ viability.

Alternatively or in addition, once removed from the donor, the organ or living tissue may be placed in a preservation solution containing the inhibitor. In addition, the kallikrein inhibitor is also preferably administered to the transplant recipient just prior to, or concommitant with, transplantation. In all cases, the inhibitor also can be administered directly to the tissue at risk, as by injection to the tissue, or it may be provided systemically, either by oral or parenteral administration, using any of the methods and formulations described herein and/or known in the art.

In one embodiment, any commercially available preservation solution may be used to advantage. Examples of such solutions include the Belzer UW solution sold under the trademark VIASPAN, described in U.S. Pat. Nos. 4,798,824, 4,873,230, 4,879,283, which are hereby incorporated by reference.

The preservation solution and perfusate composition described in the aforementioned patents includes, but is not limited to, the following:

TABLE 2

| Substance | Amount in 1 Liter |
|---|---|
| K$^+$-lactobionate | 100 mmol |
| KH$_2$PO$_4$ | 25 mmol |
| MgSO$_4$ | 5 mmol |
| Raffinose | 30 mmol |
| Adenosine | 5 mmol |
| Glutathione | 3 mmol |
| Insulin | 100 U |
| Bactrim | 0.5 mL |
| Dexamethasone | 8 mg |
| Allopurinol | 1 mM |
| Hydroxyethyl starch having a molecular weight of about 200,000 to about 300,000 daltons and a degree of substitution of from about 0.4 to 0.7 | 50 g |

The solution is brought to pH 7.4 at room temperature with NaOH. The final concentrations are Na=30.±0.5 mM, K$^+$=120±5 mM, mOsm/liter=320±5. Bactrim=trimethoprim (16 mg/mL) and sulfamethoxazole (80 mg/mL). The hydroxyethyl starch can be present in the range of from about 3 to about 8%.

This solution typically provides for a 72 hour preservation of the pancreas, 48 hour preservation for the kidney and at least 24 hour preservation for the liver. U.S. Pat. No. 5,145,771, incorporated herein by reference, described the organ preservation solution known as the "Carolina Solution," which is also useful in the present invention. The rinse or preservation solution composition described in the aforementioned patent includes, but is not limited to, the components in about the concentration ranges set forth in Table 3 below.

TABLE 3

Concentration Ranges in 1 Liter
10% modified hydroxyethyl starch 30 g/L to 100 g/L

| NaCl | 85 mM | to | 145 mM |
|---|---|---|---|
| KCl | 3 mM | to | 6 mM |
| CaCl$_2$ | 1.0 mM | to | 1.6 mM |
| KH$_2$PO$_4$ | 0.7 mM | to | 1.3 mM |
| MgSO$_4$ | 0.9 mM | to | 1.5 mM |
| Allopurinol | 0.05 mM | to | 5.0 mM |
| Desferrioxamine | 0.02 mM | to | 2.0 mM |
| Glutathione | 0.5 mM | to | 10.0 mM |
| Nicardipene | 0.1 $\mu$M | to | 5.0 $\mu$M |
| Adenosine | 0.1 mM | to | 5.0 mM |
| Fructose | 1.0 mM | to | 50.0 mM |
| Glucose | 1.0 mM | to | 50.0 mM |
| Insulin | 5 U/L | to | 250 U/L |
| Mops | 2 mM | to | 40 mM |

One specific embodiment is prepared with the components in the amounts set forth in Table 4 below in accordance with the instructions set forth below.

TABLE 4

Components of 1 Liter Rinse Solution

| 500 mL | | Distilled Deionized Water | |
|---|---|---|---|
| 50 g/L | | 10% modified hydroxyethyl starch | |
| 115 mM | | NaCl | 6.7 g |
| 5 mM | | KCl | 0.37 g |
| 1.30 mM | | CaCl$_2$ | 0.19 g |
| 1 mM | | KH$_2$PO$_4$ | 0.14 g |
| 1.2 mM | | MgSO$_4$ | 0.15 g |
| 1 mM | | Allopurinol | 0.14 g |
| 1 mM | | Desferrioxamine | 0.65 g |
| 3 mM | | Glutathione | 0.92 g |
| 2 $\mu$M | | Nicardipene | 0.80 mg |
| 1 mM | | Adenosine | 0.32 g |
| 10 mM | | Fructose | 1.8 g |
| 10 mM | | Glucose | 1.8 g |
| 100 U/L | | Insulin | 100 units |
| 20 mM | | Mops | 4.2 g |

In one embodiment this solution can be prepared as follows: using a 500 mL volumetric flask, measure 500 mL of 10% (weight/volume) hydroxyethyl starch solution and pour into a 1 L beaker. Add 400 mL of double distilled water and stir vigorously using a magnetic stir bar. Add the rest of the components one at a time. After all components are added, adjust the pH to 6.5 with 1-2 mL 5N NaOH. The solution should be stirred for at least thirty minutes. Transfer the solution to a 1 L volumetric flask and bring to 1 L final volume. Filter to remove any undissolved particles.

Still another embodiment is exemplified by Table 5 below.

TABLE 5

Concentration Ranges in 1 Liter

| NaCl | 85 mM | to | 145 mM |
|---|---|---|---|
| KCl | 3 mM | to | 6 mM |
| CaCl$_2$ | 1.0 mM | to | 1.6 mM |
| KH$_2$PO$_4$ | 0.7 mM | to | 1.3 mM |
| MgSO$_4$ | 0.9 mM | to | 1.5 mM |
| Adenosine | 0.12 mM | to | 1.2 mM |

A composition according to Table 5 above may optionally include one, several, or all of the further ingredients specified in Table 3 above. Preferably, the composition includes at least one antioxidant. Thus, one specific embodiment of a composition is set forth in Table 6 below:

TABLE 6

Components of 1 Liter Rinse Solution

| | | Distilled Deionized Water | |
|---|---|---|---|
| 500 | mL | | |
| 115 | mM | NaCl | 6.7 g |
| 5 | mM | KCl | 0.37 g |
| 1.30 | mM | CaCl$_2$ | 0.19 g |
| 1 | mM | KH$_2$PO$_4$ | 0.14 g |
| 1.2 | mM | MgSO$_4$ | 0.15 g |
| 1 | mM | Allopurinol | 0.14 g |
| 1 | mM | Desferrioxamine | 0.65 g |
| 3 | mM | Glutathione | 0.92 g |
| .12 | mM | Adenosine | 0.038 g |

Preferred compositions may further comprise one or more pharmaceutically acceptable buffers, carriers, antioxidants, protease inhibitors, or other anti-ischemia agents.

Compositions useful in the methods of the invention comprise any of the Kunitz domain polypeptides or KI polypeptides comprising such Kunitz domain polypeptides described herein. Particularly preferred are KI polypeptides comprising a Kunitz domain polypeptide having a 58-amino acid sequence of amino acids 3-60 of SEQ ID NO:2. An example of such a particularly preferred KI polypeptide useful in the methods and compositions of the invention is the PEP-1 KI polypeptide having the 60-amino acid sequence of SEQ ID NO:2. A nucleotide sequence encoding the amino acid sequence of SEQ ID NO:2 is provided in SEQ ID NO:3 (see, e.g., nucleotides 309-488 in FIG. 2). It is understood that based on the known genetic code, the invention also provides degenerate forms of the nucleotide sequence of SEQ ID NO:3 by simply substituting one or more of the known degenerate codons for each amino acid encoded by the nucleotide sequence. Nucleotides 7-180 of SEQ ID NO:3, and degenerate forms thereof, encode the non-naturally occurring Kunitz domain polypeptide having the 58-amino acid sequence of amino acids 3-60 of SEQ ID NO:2.

Concentration Considerations for KI Polypeptides

Several considerations regarding dosing with a KI polypeptide in methods of the invention may be illustrated by way of example with the representative PEP-1 KI polypeptide of the invention having the amino sequence of SEQ ID NO:2 (molecular weight of 7,054 Daltons).

Table 7, below, provides a comparison of the affinity ($K_{i,app}$) of the PEP-1 KI polypeptide for kallikrein and eleven other known plasma proteases.

TABLE 7

| Protease Substrate | PEP-1 $K_{i,app}$ (pM) | Aprotinin $K_{i,app}$ (pM) |
|---|---|---|
| human plasma kallikrein | 44 | $3.0 \times 10^4$ |
| human urine kallikrein | $>1 \times 10^8$ | $4.0 \times 10^3$ |
| porcine pancreatic kallikrein | $2.7 \times 10^7$ | 550 |
| human C1r, activated | $>2.0 \times 10^8$ | $1.0 \times 10^7$ |
| human C1s, activated | $>2.0 \times 10^7$ | $>1.0 \times 10^8$ |
| human plasma factor XIa | $1.0 \times 10^4$ | ND |
| human plasma factor XIIa | $>2.0 \times 10^7$ | $>1.0 \times 10^8$ |
| human plasmin | $1.4 \times 10^5$ | 894 |
| human pancreatic trypsin | $>2 \times 10^7$ | ND |
| human pancreatic chymotrypsin | $>2.0 \times 10^7$ | $7.3 \times 10^5$ |
| human neutrophil elastase | $>2.0 \times 10^7$ | $1.7 \times 10^6$ |
| human plasma thrombin | $>2.0 \times 10^7$ | $>1.0 \times 10^8$ |

ND = not determined

Clearly, the PEP-1 KI polypeptide is highly specific for human plasma kallikrein. Furthermore, the affinity ($K_{i,app}$) of PEP-1 for kallikrein is 1000 times higher than the affinity of aprotinin for kallikrein: the $K_{i,app}$ of PEP-1 for kallikrein is about 44 pM (Table 1), whereas the $K_{i,app}$ of aprotinin for kallikrein is 30,000 pM. Thus, a dose of PEP-1 could be approximately 1000 times lower than that used for aprotinin on a per mole basis. However, consideration of several other factors may provide a more accurate estimation of the dose of PEP-1 required in practice. Such factors include the amount of kallikrein activated upon organ removal from a particular patient, and will be recognized by the skilled artisan.

The invention will be further described with reference to the following non-limiting examples. The teachings of all the patents, patent applications and all other publications and websites cited herein are incorporated by reference in their entirety.

EXEMPLIFICATION

Example 1

A Representative KI Polypeptide

A KI polypeptide (PEP-1) useful in the compositions and methods of the invention was identified as a kallikrein binding polypeptide displayed on a recombinant phage from a phage display library. PEP-1 has the following amino acid sequence: Glu Ala Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (SEQ ID NO:2). The molecular weight of PEP-1 is 7,054 Daltons.

The nucleotide sequence (SEQ ID NO:3) of the recombinant phage DNA encoding the PEP-1 amino acid sequence (amino acids 3-60 of SEQ ID NO:2) was isolated and sequenced by standard methods determined from the recombinant phage DNA. PEP-1 was produced in amounts useful for further characterization as a recombinant protein in His4$^-$ phenotype host cells of yeast strain *Pichia pastoris*.

Example 2

Construction of a Recombinant Plasmid to Express KI Polypeptides

The initial plasmid, pHIL-D2, is ampicillin resistant and contains a wild-type allele of His4 from *P. pastoris*. The final DNA sequence comprising the coding sequence for the mata Prepro-PEP-1 fusion protein in the recombinant expression plasmid pPIC-K503 is shown in FIG. 2. The DNA sequence of pHIL-D2 was modified to produce pPIC-K503, as follows:

1. The BstBI site in the 3' AOX1 region of pHIL-D2, located downstream of the His4 gene, was removed by partial restriction digestion, fill-in, and ligation, altering the sequence from TTCGAA (SEQ ID NO:23) to TTCGCGAA (SEQ ID NO:24). This modification was made to facilitate and direct the cloning of the expression cassette into the plasmid.
2. The AatII site bearing the bla gene located downstream of His4 was removed by restriction digestion, fill-in, and ligation modifying the sequence from GACGTC (SEQ ID NO:25) to GACGTACGTC (SEQ ID NO:26). This modification was made to facilitate the cloning of expression cassettes having AatII sites into the plasmid. The DNA encoding PEP-1 was synthesized based on the nucleotide sequence from the original kallikrein-binding display phage and consisted of 450 base pairs (bp). The final DNA sequence of the insert in the pHIL-D2 plasmid is flanked by a 5' AOX1 sequence and a 3' AOX1 sequence (portions of which are shown in FIG. 2) and encode a fusion protein comprising the mata prepro signal peptide of *S. cerevisiae* fused to the structural coding sequence for the PEP-1 KI polypeptide. The signal peptide was added to facilitate the secretion of PEP-1 from the yeast host cells. The oligonucleotides to form the insert were synthesized and obtained commercially (Genesis Labs, The Woodlands, Tex.), and the insert was generated by polymerase chain reaction (PCR). The linked synthetic DNA encoding the mata prepro/PEP-1 fusion protein was then incorporated by ligation into the modified pHIL-D2 plasmid between the BstBI and EcoRI sites.

The ligation products were used to transform *Escherichia coli* strain XL1 Blue. A PCR assay was used to screen *E. coli* transformants for the desired plasmid construct. DNA from cell extracts was amplified by PCR using primers containing the 5' AOX1 and 3' AOX1 sequences (see above and FIG. 2). PCR products of the correct number of base pairs were sequenced. In addition, approximately 20-50 by on either side of the cloning sites were sequenced, and the predicted sequence was obtained. The final DNA sequence of the insert in the pHIL-D2 plasmid (to yield plasmid pPIC-K503) is shown in FIG. 2 along with portions of flanking 5' and 3' AOX1 sequences and corresponding amino acid sequence of the fusion protein comprising the mata prepro signal peptide of *S. cerevisiae* fused to the structural coding sequence for the PEP-1 KI polypeptide. A transformant with the desired expression plasmid construct, plasmid pPIC-K503, was selected for preparing yeast cell lines for routine production of PEP-1.

Example 3

Manufacture of PEP-1 from Recombinant Yeast Cell Line

Spheroplasts of *P. pastoris* GS115 having the His4$^-$ phenotype were transformed with the expression plasmid pPIC-K503 (above) following linearization of the plasmid at the SacI site and homologous recombination of the plasmid DNA into the host 5' AOX1 locus. The phenotype of the production strain is His4$^+$. The entire plasmid was inserted into the 5' AOX1 genomic sequence of the yeast.

Isolates from the transformation were screened for growth in the absence of exogenous histidine with methanol as the sole carbon source. Greater than 95% of the transformants retained the wild-type ability to grow with methanol as the sole carbon source, thereby demonstrating that the plasmid had been inserted into the host genome by homologous recombination rather than transplacement. These transformants did not require exogenous histidine for growth, thereby demonstrating that the plasmid had integrated into the host genome. Selected colonies were cloned. Small culture expression studies were performed to identify clones secreting the highest levels of active PEP-1 into the culture medium. PEP-1 secretion levels in clarified culture supernatant solutions were quantified for PEP-1 levels by sodium dodecyl sulfate polyacrylamide gel electrophoresis (SDS-PAGE) and evaluated for kallikrein inhibition. A yeast clone was selected for PEP-1 production based on its high level of PEP-1 expression among cultures sampled.

Master and working cell banks of *P. pastoris* producing PEP-1 were prepared commercially (MDS Pharma Services, Bothell, Wash.). A standard production of PEP-1 in yeast comprised three steps as follows: (1) preparation of the seed culture, (2) fermentation, and (3) recovery of the culture.

The seed culture step consisted of the inoculation of six flasks (300 mL each) containing sterile inoculum broth (yeast nitrogen base, potassium phosphate, and glycerol, pH=5) with the contents of a single vial of a working cell bank of *P. pastoris* producing PEP-1. Flasks were inoculated in an orbital shaker (300 rpm) for approximately 13 hours at 30° C.±2° C.

Fermentations were performed in a closed 100 liter Braun fermenter filled with sterile broth. Each fermentation was initiated with the transfer of the contents of the six seed culture flasks to the fermenter. After approximately 24 hours, the glycerol in the fermenter became exhausted and additional glycerol was added for approximately 8 additional hours.

A mixed feed phase, which lasted approximately 83 hours, was then initiated by the addition of a glycerol and methanol feed. At the end of this time, the fermentation was terminated, and the fermenter contents were diluted with purified water. The purification and processing of PEP-1 consisted of five steps as follows: (1) expanded bed chromatography, (2) cation exchange chromatography, (3) hydrophobic interaction chromatography (HIC), (4) ultrafiltration and diafiltration, and (5) final filtration and packaging.

The initial purification step consisted of expanded bed chromatography. The diluted fermenter culture was applied to the equilibrated column packed with Streamline SP resin (Amersham Pharmacia Streamline 200 chromatography column, Amersham Pharmacia, Piscataway, N.J.). The column was then washed (50 mM acetic acid, pH=3.0-3.5) in an up-flow mode to flush the yeast cells from the expanded bed. The top adaptor was raised above the expanded bed enhance washing. The flow was stopped and the bed was allowed to settle. The adaptor was moved down so that it was slightly above the settled bed. The direction of the flow was reversed. The effluent was collected. Washing was continued in a downward mode using 50 mM sodium acetate, pH 4.0. The effluent was collected. PEP-1 was eluted from the column using 50 mM sodium acetate, pH 6.0. The eluate was collected in a 50 liter container. The eluate was then filtered through a 0.22 m filter into a clean container located in the purification site. Additional samples were collected for the determination of PEP-1 concentration. A cation exchange chromatography step was then performed using the filtered eluate from the expanded bed column. PEP-1 was eluted from the column using 15 mM trisodium citrate, pH 6.2.

Additional proteins were removed from the PEP-1 preparation by hydrophobic interaction chromatography (HIC). Prior to HIC, the eluate from the cation exchange column was diluted with ammonium sulfate. The eluate was applied to the column, and the PEP-1 was eluted using ammonium sulfate (0.572 M) in potassium phosphate (100 mM), pH 7.0. The eluate was collected in fractions based on A280 values. All fractions were collected into sterile, pre-weighed PETG bottles.

Selected fractions were pooled into a clean container. The pool was concentrated by ultrafiltration. The concentrated PEP-1 preparation was immediately diafiltered against ten volumes of PBS, pH 7.0.

A final filtration step was performed prior to packaging in order to minimize the bioburden in the bulk PEP-1. The bulk solution was filtered through a 0.22 m filter and collected into a sterile, pre-weighed PETG bottle. A sample was removed for lot release testing. The remainder of the bulk was dispensed aseptically into sterile PETG bottles and stored at −20° C.

Example 4

Kallikrein Inhibition Assay

A kinetic test was used to measure inhibitory activity of KI polypeptides, such as PEP-1. The kinetic assay measures fluorescence following kallikrein-mediated cleavage of a substrate, prolylphenylalanylarginyl amino methyl coumarin. A known amount of kallikrein was incubated with a serially diluted KI polypeptide reference standard or serially diluted KI polypeptide test samples, in a suitable reaction buffer on a microtiter plate. Each sample was run in triplicate. The substrate solution was added, and the plate read immediately using an excitation wavelength of 360 nm and an emission wavelength of 460 nm. At least two each of the reference standard and sample curves were required to have an R-squared value of 0.95 to be considered valid.

Example 5

Organ Preservation

HUVEC at confluence were washed in PBS and further incubated at 4 degrees for 24-48 hours in a serum free medium (SFM). After cold storage, cells were washed several times with PBS, and kallikrein (0.125 U) and the specific kallikrein substrate S2302 were added to the cells. Changes in optical density were recorded. For light microscopy evaluation of cell-bound PEP-1, after cold storage, HUVEC were treated with PEP-1, formalin fixed and treated with rabbit anti-PEP-1 and peroxidase conjugated anti-rabbit IgG. The ability of HUVEC to produce kallikrein was also evaluated on cell surface and in the supernatants of cells maintained at 37° C. Kallikrein activity was 380±19 A.U. in supernatants of HUVEC maintained at 37° C.; no activity was measurable on the surface of the same cells. At light microscopy evaluation there was significant binding of PEP-1 to the surface of HUVEC cold treated for 24 hours. The maximum of the binding was obtained by incubating cells in presence of PEP-1 (5 mg/ml). Cell-bound PEP-1 retained the ability to inhibit exogenous kallikrein. These results indicate that PEP-1 binds to endothelial cells, maintaining its kallikrein inhibitory activity. Therefore it can be used to detect and modulate kinin-mediated damage on the vascular surface.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for reducing kallikrein activity in a removed organ or tissue, the method comprising: contacting the organ or tissue, ex vivo, with an effective amount of a polypeptide comprising amino acids 3-60 of SEQ ID NO: 2.

2. The method of claim 1, wherein the polypeptide comprises SEQ ID NO: 2.

3. The method of claim 1, wherein the organ or tissue is selected from the group consisting of heart, lung, kidney, pancreas, liver, intestine, endothelial tissue, vascular tissue and skin.

4. The method of claim 1, wherein the polypeptide consists of amino acids 3-60 of SEQ ID NO: 2.

5. The method of claim 1, wherein the polypeptide consists of SEQ ID NO: 2.

6. A method for reducing reperfusion injury in a removed organ or tissue, the method comprising: contacting the organ or tissue, ex vivo, with an effective amount of a polypeptide comprising amino acids 3-60 of SEQ ID NO: 2.

7. The method of claim 6, wherein the polypeptide comprises SEQ ID NO: 2.

8. The method of claim 6, wherein the organ or tissue is selected from the group consisting of heart, lung, kidney, pancreas, liver, intestine, endothelial tissue, vascular tissue and skin.

9. The method of claim 6, wherein the polypeptide consists of amino acids 3-60 of SEQ ID NO: 2.

10. The method of claim 6, wherein the polypeptide consists of SEQ ID NO: 2.

* * * * *

```
                        SEQUENCE LISTING

<160> NUMBER OF SEQ ID NOS: 41

<210> SEQ ID NO 1
<211> LENGTH: 58
<212> TYPE: PRT
<213> ORGANISM: Artificial Sequence
<220> FEATURE:
<223> OTHER INFORMATION: Polypeptide Inhibiting Kallikrein
<220> FEATURE:
<221> NAME/KEY: VARIANT
<222> LOCATION: 1, 2, 3, 4, 6, 7, 8, 9, 20, 24, 25, 26, 27, 28, 29,  41,
      42, 44, 46, 47, 48, 49, 50, 52, 53, 54, 56, 57, 58
<223> OTHER INFORMATION: Xaa = Any Amino Acid
<220> FEATURE:
<221> NAME/KEY: VARIANT
<222> LOCATION: 10
<223> OTHER INFORMATION: Xaa = Asp or Glu
<220> FEATURE:
<221> NAME/KEY: VARIANT
<222> LOCATION: 11
<223> OTHER INFORMATION: Xaa = Asp, Gly, Ser, Val, Asn, Ile, Ala or Thr
<220> FEATURE:
<221> NAME/KEY: VARIANT
<222> LOCATION: 13
<223> OTHER INFORMATION: Xaa = Arg, His, Pro, Asn, Ser, Thr, Ala, Gly,
      Lys or Gln
<220> FEATURE:
<221> NAME/KEY: VARIANT
<222> LOCATION: 15
<223> OTHER INFORMATION: Xaa = Arg, Lys, Ala, Ser, Gly, Met, Asn or Gln
<220> FEATURE:
<221> NAME/KEY: VARIANT
<222> LOCATION: (16)...(16)
<223> OTHER INFORMATION: Xaa = Ala, Gly, Ser, Asp or Asn
<220> FEATURE:
<221> NAME/KEY: VARIANT
<222> LOCATION: (17)...(17)
<223> OTHER INFORMATION: Xaa = Ala, Asn, Ser, Ile, Gly, Val, Gln or Thr
<220> FEATURE:
<221> NAME/KEY: VARIANT
<222> LOCATION: (18)...(18)
<223> OTHER INFORMATION: Xaa = His, Leu, Gln or Ala
<220> FEATURE:
<221> NAME/KEY: VARIANT
<222> LOCATION: (19)...(19)
```

```
<223> OTHER INFORMATION: Xaa = Pro, Gln, Leu, Asn or Ile
<220> FEATURE:
<221> NAME/KEY: VARIANT
<222> LOCATION: (21)...(21)
<223> OTHER INFORMATION: Xaa = Trp, Phe, Tyr, His or Ile
<220> FEATURE:
<221> NAME/KEY: VARIANT
<222> LOCATION: (22)...(23)
<223> OTHER INFORMATION: Xaa = Tyr or Phe
<220> FEATURE:
<221> NAME/KEY: VARIANT
<222> LOCATION: (31)...(31)
<223> OTHER INFORMATION: Xaa = Glu, Asp, Gln, Asn, Ser, Ala, Val, Leu,
     Ile or Thr
<220> FEATURE:
<221> NAME/KEY: VARIANT
<222> LOCATION: (32)...(32)
<223> OTHER INFORMATION: Xaa = Glu, Gln, Asp, Asn, Pro, Thr, Leu, Ser,
     Ala, Gly or Val
<220> FEATURE:
<221> NAME/KEY: VARIANT
<222> LOCATION: (34)...(34)
<223> OTHER INFORMATION: Xaa = Thr, Ile, Ser, Val, Ala, Asn, Gly or Leu
<220> FEATURE:
<221> NAME/KEY: VARIANT
<222> LOCATION: (35)...(35)
<223> OTHER INFORMATION: Xaa = Tyr, Trp or Phe
<220> FEATURE:
<221> NAME/KEY: VARIANT
<222> LOCATION: (39)...(39)
<223> OTHER INFORMATION: Xaa = Glu, Gly, Ala, Ser or Asp
<220> FEATURE:
<221> NAME/KEY: VARIANT
<222> LOCATION: (40)...(40)
<223> OTHER INFORMATION: Xaa = Gly or Ala
<220> FEATURE:
<221> NAME/KEY: VARIANT
<222> LOCATION: (43)...(43)
<223> OTHER INFORMATION: Xaa = Asn or Gly
<220> FEATURE:
<221> NAME/KEY: VARIANT
<222> LOCATION: (45)...(45)
<223> OTHER INFORMATION: Xaa = Phe or Tyr

<400> SEQUENCE: 1

Xaa Xaa Xaa Xaa Cys Xaa Xaa Xaa Xaa Xaa Gly Xaa Cys Xaa Xaa
 1               5                  10                  15

Xaa Xaa Xaa Xaa Xaa Xaa Xaa Xaa Xaa Xaa Xaa Xaa Xaa Cys Xaa Xaa
                20                  25                  30

Phe Xaa Xaa Gly Gly Cys Xaa Xaa Xaa Xaa Xaa Xaa Xaa Xaa Xaa
            35                  40                  45

Xaa Xaa Cys Xaa Xaa Xaa Cys Xaa Xaa Xaa
    50                  55

<210> SEQ ID NO 2
<211> LENGTH: 60
<212> TYPE: PRT
<213> ORGANISM: Artificial Sequence
<220> FEATURE:
<223> OTHER INFORMATION: Isolated Binding Peptides

<400> SEQUENCE: 2

Glu Ala Met His Ser Phe Cys Ala Phe Lys Ala Asp Asp Gly Pro Cys
 1               5                  10                  15

Arg Ala Ala His Pro Arg Trp Phe Phe Asn Ile Phe Thr Arg Gln Cys
                20                  25                  30

Glu Glu Phe Ile Tyr Gly Gly Cys Glu Gly Asn Gln Asn Arg Phe Glu
            35                  40                  45

Ser Leu Glu Glu Cys Lys Lys Met Cys Thr Arg Asp
    50                  55                  60
```

```
<210> SEQ ID NO 3
<211> LENGTH: 179
<212> TYPE: DNA
<213> ORGANISM: Artificial Sequence
<220> FEATURE:
<223> OTHER INFORMATION: Coding Sequence of Pep-1

<400> SEQUENCE: 3
gaggctatgc actctttctg tgctttcaag gctgacgacg gtcgtgcaga gctgctcacc      60
caagatggtt cttcaacatc ttcacgcgtc aatgcgagga gttcatctac ggtggttgtg     120
agggtaacca aaacagattc gagtctctag aggagtgtaa aagatgtgt actagagac     179

<210> SEQ ID NO 4
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 4

Met His Ser Phe Cys Ala Phe Lys Ala Asp Asp Gly Pro Cys Lys Ala
1               5                   10                  15

Asn His Leu Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 5
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 5

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
            20                  25                  30

Phe Thr Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 6
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 6

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Gln
            20                  25                  30

Phe Thr Tyr Gly Gly Cys Ala Gly Asn Gln Asn Arg Phe Glu Ser Leu
        35                  40                  45

Glu Glu Cys Lys Lys Met Cys Thr Arg Asp
```

<210> SEQ ID NO 7
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 7

Met His Ser Phe Cys Ala Phe Lys Ala Asp Asp Gly His Cys Lys Ala
1               5                   10                  15

Ser Leu Pro Arg Phe Phe Asn Ile Phe Thr Arg Gln Cys Glu Glu
            20                  25                  30

Phe Ile Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 8
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 8

Met His Ser Phe Cys Ala Phe Lys Ala Asp Asp Gly His Cys Lys Ala
1               5                   10                  15

Asn His Gln Arg Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 9
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 9

Met His Ser Phe Cys Ala Phe Lys Ala Asp Asp Gly His Cys Lys Gly
1               5                   10                  15

Ala His Leu Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

<210> SEQ ID NO 10
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 10

Met His Ser Phe Cys Ala Phe Lys Ala Asp Asp Gly Arg Cys Lys Gly
1               5                   10                  15

```
Ala His Leu Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

<210> SEQ ID NO 11
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 11

Met His Ser Phe Cys Ala Phe Lys Ala Asp Gly Gly Arg Cys Arg Gly
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 12
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 12

Met His Ser Phe Cys Ala Phe Lys Ala Asp Asp Gly Pro Cys Arg Ala
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 13
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 13

Met His Ser Phe Cys Ala Phe Lys Ala Asp Val Gly Arg Cys Arg Gly
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 14
<211> LENGTH: 58
<212> TYPE: PRT
```

```
<213> ORGANISM: Artificial Sequence
<220> FEATURE:
<223> OTHER INFORMATION: Isolated Binding Peptides

<400> SEQUENCE: 14

Met His Ser Phe Cys Ala Phe Lys Ala Asp Val Gly Arg Cys Arg Gly
1               5                   10                  15

Ala Gln Pro Arg Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 15
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 15

Met His Ser Phe Cys Ala Phe Lys Ala Asp Asp Gly Ser Cys Arg Ala
1               5                   10                  15

Ala His Leu Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 16
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 16

Met His Ser Phe Cys Ala Phe Lys Ala Glu Gly Gly Ser Cys Arg Ala
1               5                   10                  15

Ala His Gln Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 17
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 17

Met His Ser Phe Cys Ala Phe Lys Ala Asp Asp Gly Pro Cys Arg Gly
1               5                   10                  15

Ala His Leu Arg Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45
```

```
Glu Glu Cys Lys Lys Met Cys Thr Arg Asp
    50                  55
```

<210> SEQ ID NO 18
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 18

```
Met His Ser Phe Cys Ala Phe Lys Ala Asp Asp Gly His Cys Arg Gly
  1               5                  10                  15

Ala Leu Pro Arg Trp Phe Phe Asn Ile Phe Thr Arg Gln Cys Glu Glu
             20                  25                  30

Phe Ser Tyr Gly Gly Cys Gly Gly Asn Gln Asn Arg Phe Glu Ser Leu
         35                  40                  45

Glu Glu Cys Lys Lys Met Cys Thr Arg Asp
    50                  55
```

<210> SEQ ID NO 19
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 19

```
Met His Ser Phe Cys Ala Phe Lys Ala Asp Ser Gly Asn Cys Arg Gly
  1               5                  10                  15

Asn Leu Pro Arg Phe Phe Phe Asn Ile Phe Thr Arg Gln Cys Glu Glu
             20                  25                  30

Phe Ser Tyr Gly Gly Cys Gly Gly Asn Gln Asn Arg Phe Glu Ser Leu
         35                  40                  45

Glu Glu Cys Lys Lys Met Cys Thr Arg Asp
    50                  55
```

<210> SEQ ID NO 20
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 20

```
Met His Ser Phe Cys Ala Phe Lys Ala Asp Ser Gly Arg Cys Arg Gly
  1               5                  10                  15

Asn His Gln Arg Phe Phe Phe Asn Ile Phe Thr Arg Gln Cys Glu Glu
             20                  25                  30

Phe Ser Tyr Gly Gly Cys Gly Gly Asn Gln Asn Arg Phe Glu Ser Leu
         35                  40                  45

Glu Glu Cys Lys Lys Met Cys Thr Arg Asp
    50                  55
```

<210> SEQ ID NO 21
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 21

```
Met His Ser Phe Cys Ala Phe Lys Ala Asp Gly Gly Arg Cys Arg Ala
1               5                   10                  15

Ile Gln Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55
```

<210> SEQ ID NO 22
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 22

```
Met His Ser Phe Cys Ala Phe Lys Ala Asp Asp Gly Arg Cys Arg Gly
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55
```

<210> SEQ ID NO 23
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 23

```
Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55
```

<210> SEQ ID NO 24
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 24

```
Met His Ser Phe Cys Ala Phe Lys Ala Asp Asp Gly His Cys Lys Ala
1               5                   10                  15

Ser Leu Pro Arg Phe Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55
```

<210> SEQ ID NO 25

```
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 25

Met His Ser Phe Cys Ala Phe Lys Ala Asp Asp Gly Pro Cys Lys Ala
1               5                   10                  15

Asn His Leu Arg Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 26
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 26

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
            20                  25                  30

Phe Thr Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 27
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 27

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Gln
            20                  25                  30

Phe Thr Tyr Gly Gly Cys Ala Gly Asn Gln Asn Arg Phe Glu Ser Leu
        35                  40                  45

Glu Glu Cys Lys Lys Met Cys Thr Arg Asp
    50                  55

<210> SEQ ID NO 28
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 28

Met His Ser Phe Cys Ala Phe Lys Ala Asp Asp Gly His Cys Lys Ala
1               5                   10                  15

Ser Leu Pro Arg Phe Phe Phe Asn Ile Phe Thr Arg Gln Cys Glu Glu
            20                  25                  30
```

```
Phe Ile Tyr Gly Gly Cys Gly Gly Asn Gln Asn Arg Phe Glu Ser Leu
         35                  40                  45

Glu Glu Cys Lys Lys Met Cys Thr Arg Asp
 50                  55

<210> SEQ ID NO 29
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 29

Met His Ser Phe Cys Ala Phe Lys Ala Asp Asp Gly His Cys Lys Ala
 1               5                  10                  15

Asn His Gln Arg Phe Phe Phe Asn Ile Phe Thr Arg Gln Cys Glu Glu
                 20                  25                  30

Phe Ser Tyr Gly Gly Cys Gly Gly Asn Gln Asn Arg Phe Glu Ser Leu
         35                  40                  45

Glu Glu Cys Lys Lys Met Cys Thr Arg Asp
 50                  55

<210> SEQ ID NO 30
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 30

Met His Ser Phe Cys Ala Phe Lys Ala Asp Asp Gly His Cys Lys Ala
 1               5                  10                  15

Asn His Gln Arg Phe Phe Phe Asn Ile Phe Thr Arg Gln Cys Glu Glu
                 20                  25                  30

Phe Ser Tyr Gly Gly Cys Gly Gly Asn Gln Asn Arg Phe Glu Ser Leu
         35                  40                  45

Glu Glu Cys Lys Lys Met Cys Thr Arg Asp
 50                  55

<210> SEQ ID NO 31
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 31

Met His Ser Phe Cys Ala Phe Lys Ala Asp Asp Gly His Cys Lys Ala
 1               5                  10                  15

Asn His Gln Arg Phe Phe Phe Asn Ile Phe Thr Arg Gln Cys Glu Glu
                 20                  25                  30

Phe Ser Tyr Gly Gly Cys Gly Gly Asn Gln Asn Arg Phe Glu Ser Leu
         35                  40                  45

Glu Glu Cys Lys Lys Met Cys Thr Arg Asp
 50                  55

<210> SEQ ID NO 32
<211> LENGTH: 58
<212> TYPE: PRT
<213> ORGANISM: Artificial Sequence
<220> FEATURE:
<223> OTHER INFORMATION: Isolated Binding Peptides
```

-continued

```
<400> SEQUENCE: 32

Met His Ser Phe Cys Ala Phe Lys Ala Asp Asp Gly His Cys Lys Ala
1               5                   10                  15

Asn His Gln Arg Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 33
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 33

Met His Ser Phe Cys Ala Phe Lys Ala Asp Asp Gly His Cys Lys Gly
1               5                   10                  15

Ala His Leu Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

<210> SEQ ID NO 34
<211> LENGTH: 58
<212> TYPE: PRT
<213> ORGANISM: Artificial Sequence
<220> FEATURE:
<223> OTHER INFORMATION: Isolated Binding Peptides

<400> SEQUENCE: 34

Met His Ser Phe Cys Ala Phe Lys Ala Asp Asp Gly Pro Cys Lys Ala
1               5                   10                  15

Ile Met Lys Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

<210> SEQ ID NO 35
<211> LENGTH: 548
<212> TYPE: DNA
<213> ORGANISM: Artificial Sequence
<220> FEATURE:
<223> OTHER INFORMATION: Coding sequence for fusion protein
<220> FEATURE:
<221> NAME/KEY: CDS
<222> LOCATION: (54)...(488)

<400> SEQUENCE: 35 cgactttta  cgacaacttg agaagatcaa aaacaacta attattcgaa acg atg         56
                                                          Met
                                                          1 aga ttc cca tct atc ttc act gct gtt ttg ttc gct gct tcc tct gct      104
Arg Phe Pro Ser Ile Phe Thr Ala Val Leu Phe Ala Ala Ser Ser Ala
            5                   10                  15 ttg gct gct cca gtt aac acc act act gaa gac gag act gct caa att     152
```

```
Leu Ala Ala Pro Val Asn Thr Thr Thr Glu Asp Glu Thr Ala Gln Ile
         20                  25                  30 cct gct gag gct gtc atc ggt tac tct gac ttg gaa ggt gac ttc gac      200
Pro Ala Glu Ala Val Ile Gly Tyr Ser Asp Leu Glu Gly Asp Phe Asp
         35                  40                  45 gtc gct gtt ttg cca ttc tct aac tct act aac aac ggt ttg ttg ttc      248
Val Ala Val Leu Pro Phe Ser Asn Ser Thr Asn Asn Gly Leu Leu Phe
 50                  55                  60                  65 atc aac act acc atc gct tct atc gct gct aag gag gaa ggt gtt tcc      296
Ile Asn Thr Thr Ile Ala Ser Ile Ala Ala Lys Glu Glu Gly Val Ser
                 70                  75                  80 ctc gag aag aga gag gct atg cac tct ttc tgt gct ttc aag gct gac      344
Leu Glu Lys Arg Glu Ala Met His Ser Phe Cys Ala Phe Lys Ala Asp
             85                  90                  95 gac ggt ccg tgc aga gct gct cac cca aga tgg ttc ttc aac atc ttc      392
Asp Gly Pro Cys Arg Ala Ala His Pro Arg Trp Phe Phe Asn Ile Phe
        100                 105                 110 acg cgt caa tgc gag gag ttc atc tac ggt ggt tgt gag ggt aac caa      440
Thr Arg Gln Cys Glu Glu Phe Ile Tyr Gly Gly Cys Glu Gly Asn Gln
    115                 120                 125 aac aga ttc gag tct cta gag gag tgt aag aag atg tgt act aga gac      488
Asn Arg Phe Glu Ser Leu Glu Glu Cys Lys Lys Met Cys Thr Arg Asp
130                 135                 140                 145 tagtaagaat tcgccttaga catgactgtt cctcagttca agttgggcac ttacgagaag   548

<210> SEQ ID NO 36
<211> LENGTH: 58
<212> TYPE: PRT
<213> ORGANISM: Artificial Sequence
<220> FEATURE:
<223> OTHER INFORMATION: Isolated Binding Peptide
<220> FEATURE:
<221> NAME/KEY: VARIANT
<222> LOCATION: 10
<223> OTHER INFORMATION: Xaa = Asp or Glu
<220> FEATURE:
<221> NAME/KEY: VARIANT
<222> LOCATION: 11
<223> OTHER INFORMATION: Xaa = Asp, Gly, Ser, Val, Asn, Ile, Ala or Thr
<220> FEATURE:
<221> NAME/KEY: VARIANT
<222> LOCATION: 13
<223> OTHER INFORMATION: Xaa = Arg, His, Pro, Asn, Ser, Thr, Ala, Gly,
      Lys or Gln
<220> FEATURE:
<221> NAME/KEY: VARIANT
<222> LOCATION: 15
<223> OTHER INFORMATION: Xaa = Arg, Lys, Ala, Ser, Gly, Met, Asn or Gln
<220> FEATURE:
<221> NAME/KEY: VARIANT
<222> LOCATION: 16
<223> OTHER INFORMATION: Xaa = Ala, Gly, Ser, Asp or Asn
<220> FEATURE:
<221> NAME/KEY: VARIANT
<222> LOCATION: (17)...(17)
<223> OTHER INFORMATION: Xaa = Ala, Asn, Ser, Ile, Gly, Val, Gln or Thr
<220> FEATURE:
<221> NAME/KEY: VARIANT
<222> LOCATION: (18)...(18)
<223> OTHER INFORMATION: Xaa = His, Leu, Gln or Ala
<220> FEATURE:
<221> NAME/KEY: VARIANT
<222> LOCATION: (19)...(19)
<223> OTHER INFORMATION: Xaa = Pro, Gln, Leu, Asn or Ile
<220> FEATURE:
<221> NAME/KEY: VARIANT
<222> LOCATION: (21)...(21)
<223> OTHER INFORMATION: Xaa = Trp, Phe, Tyr, His or Ile
<220> FEATURE:
<221> NAME/KEY: VARIANT
<222> LOCATION: (31)...(31)
```

```
<223> OTHER INFORMATION: Xaa = Glu, Asp, Gln, Asn, Ser, Ala, Val, Leu,
      Ile or Thr
<220> FEATURE:
<221> NAME/KEY: VARIANT
<222> LOCATION: (32)...(32)
<223> OTHER INFORMATION: Xaa = Glu, Gln, Asp, Asn, Pro, Thr, Leu, Ser,
      Ala, Gly or Val
<220> FEATURE:
<221> NAME/KEY: VARIANT
<222> LOCATION: (34)...(34)
<223> OTHER INFORMATION: Xaa = Thr, Ile, Ser, Val, Ala, Asn, Gly or Leu
<220> FEATURE:
<221> NAME/KEY: VARIANT
<222> LOCATION: (35)...(35)
<223> OTHER INFORMATION: Xaa = Tyr, Trp or Phe
<220> FEATURE:
<221> NAME/KEY: VARIANT
<222> LOCATION: (39)...(39)
<223> OTHER INFORMATION: Xaa = Glu, Gly, Ala, Ser or Asp

<400> SEQUENCE: 36

Met His Ser Phe Cys Ala Phe Lys Ala Xaa Xaa Gly Xaa Cys Xaa Xaa
  1               5                  10                  15

Xaa Xaa Xaa Arg Xaa Phe Phe Asn Ile Phe Thr Arg Gln Cys Xaa Xaa
             20                  25                  30

Phe Xaa Xaa Gly Gly Cys Xaa Gly Asn Gln Asn Arg Phe Glu Ser Leu
         35                  40                  45

Glu Glu Cys Lys Lys Met Cys Thr Arg Asp
         50                  55

<210> SEQ ID NO 37
<211> LENGTH: 6
<212> TYPE: DNA
<213> ORGANISM: Artificial Sequence
<220> FEATURE:
<223> OTHER INFORMATION: Modified Cloning Site

<400> SEQUENCE: 37 ttcgaa                                                              6

<210> SEQ ID NO 38
<211> LENGTH: 8
<212> TYPE: DNA
<213> ORGANISM: Artificial Sequence
<220> FEATURE:
<223> OTHER INFORMATION: Modified Cloning Site

<400> SEQUENCE: 38 ttcgcgaa                                                            8

<210> SEQ ID NO 39
<211> LENGTH: 6
<212> TYPE: DNA
<213> ORGANISM: Artificial Sequence
<220> FEATURE:
<223> OTHER INFORMATION: Modified Cloning Site

<400> SEQUENCE: 39 gacgtc                                                              6

<210> SEQ ID NO 40
<211> LENGTH: 10
<212> TYPE: DNA
<213> ORGANISM: Artificial Sequence
<220> FEATURE:
<223> OTHER INFORMATION: Modified Cloning Site

<400> SEQUENCE: 40
```

-continued

```
gacgtacgtc                                                          10
```

<210> SEQ ID NO 41
<211> LENGTH: 145
<212> TYPE: PRT
<213> ORGANISM: Artificial Sequence
<220> FEATURE:
<223> OTHER INFORMATION: Fusion Protein

<400> SEQUENCE: 41

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Met His Ser Phe Cys Ala Phe Lys Ala
                85                  90                  95

Asp Asp Gly Pro Cys Arg Ala Ala His Pro Arg Trp Phe Phe Asn Ile
                100                 105                 110

Phe Thr Arg Gln Cys Glu Glu Phe Ile Tyr Gly Gly Cys Glu Gly Asn
            115                 120                 125

Gln Asn Arg Phe Glu Ser Leu Glu Glu Cys Lys Lys Met Cys Thr Arg
        130                 135                 140

Asp
145
```